United States Patent
Feligioni et al.

(10) Patent No.: US 10,398,756 B2
(45) Date of Patent: Sep. 3, 2019

(54) CELL-PERMEABLE PEPTIDE SYSTEM FOR TREATING DISEASES CAUSED BY GLUTAMATE EXCITOTOXICITY

(71) Applicants: Marco Feligioni, Savona (IT); Robert Giovanni Nistico', Rome (IT)

(72) Inventors: Marco Feligioni, Savona (IT); Robert Giovanni Nistico', Rome (IT)

( * ) Notice: Subject to any disclaimer, the term of this patent is extended or adjusted under 35 U.S.C. 154(b) by 0 days.

(21) Appl. No.: 15/657,238

(22) Filed: Jul. 24, 2017

(65) Prior Publication Data

US 2017/0340701 A1 Nov. 30, 2017

Related U.S. Application Data

(62) Division of application No. 15/301,760, filed as application No. PCT/IB2015/051640 on Mar. 6, 2015, now Pat. No. 9,901,618.

(30) Foreign Application Priority Data

Apr. 4, 2014 (IT) .............................. RM2014A0171

(51) Int. Cl.
| | | |
|---|---|---|
| *A61K 38/16* | (2006.01) | |
| *A61K 38/17* | (2006.01) | |
| *C07K 14/705* | (2006.01) | |
| *A61P 43/00* | (2006.01) | |
| *A61K 38/00* | (2006.01) | |
| *C07K 14/005* | (2006.01) | |
| *C12N 15/70* | (2006.01) | |

(52) U.S. Cl.
CPC ............ *A61K 38/177* (2013.01); *A61K 38/00* (2013.01); *A61K 38/162* (2013.01); *C07K 14/005* (2013.01); *C07K 14/705* (2013.01); *C12N 15/70* (2013.01); *C07K 2319/10* (2013.01); *C12N 2740/16322* (2013.01); *C12N 2800/101* (2013.01); *Y02A 50/473* (2018.01)

(58) Field of Classification Search
CPC ................ C07K 14/705; C07K 14/005; C07K 2319/10; A61K 38/00; A61K 38/177; A61K 38/162; C12N 2740/16322; C12N 15/70; C12N 2800/101; Y02A 50/473
See application file for complete search history.

(56) References Cited

U.S. PATENT DOCUMENTS

2008/0248490 A1 10/2008 Polakiewicz et al.
2010/0273702 A1 10/2010 Chinea Santiago et al.

FOREIGN PATENT DOCUMENTS

WO 2014057484 4/2014

OTHER PUBLICATIONS

Bonny, C. et al., "Cell-Permeable Peptide Inhibitors of JNK Novel Blockers of β-Cell Death," Diabetes, American Diabetes Association, vol. 50, Jan. 2001, pp. 77-82.
Borsello, T. et al., "A Peptide Inhibitor of C-Jun N-Terminal Kinase Protects Against Excitotoxicity and Cerebral Ischemia," Nature Medicine, Nature Publishing Group, vol. 9, No. 9, Sep. 2003, pp. 1180-1186.
Feligioni, M. et al., "Crosstalk between JNK and SUMO Signaling Pathways: deSUMOylation is Protective Against H2O2-Induced Cell Injury," PLOS ONE, vol. 6, No. 12, Dec. 2011, pp. 1-9.
Feligioni, M. et al.: "NMDA Receptor-Dependent Glutamate Release is Controlled Bypresynaptic JNK2," 36° Congresso Nazionale Della Societa Italiana Di Farmacologia, Sep. 10, 2014, p. 1.
Kaoud et al., "Development of JNK2-Selective Peptide Inhibitors that Inhibit Breast Cancer cell Migration," ACS Chemical Biology, vol. 6, No. 6, Jun. 17, 2011, pp. 658-666 Abstract only.
Database Uniprot [Online], "RecName: Full=Syntaxin-1A; AltName: Full=Neuron-Specific Antigen HPC-1,", accessed Aug. 8, 2017, pp. 1-10.
Italian Search Report issued in Application No. IT RM20140171, dated Nov. 21, 2014.
International Search Report issued in Application No. PCT/IB2015/051640, dated Jun. 8, 2015.

*Primary Examiner* — Karlheinz R. Skowronek
*Assistant Examiner* — Li N Komatsu
(74) *Attorney, Agent, or Firm* — Young & Thompson

(57) ABSTRACT

Peptide system including at least one peptide blocking the presynaptic release of glutamate. The peptide has the sequence SEQ ID NO 5: GRKKRRQRRRP-PIEQSIEQEEGLNRS and/or sequence SEQ ID NO 8: GRKKRRQRRRPPMSEYNATQSDYRER for use in treating pathologies associated with glutamate excitotoxicity.

6 Claims, 13 Drawing Sheets
Specification includes a Sequence Listing.

CELL-PERMEABLE PEPTIDE SYSTEM FOR TREATING DISEASES CAUSED BY GLUTAMATE EXCITOTOXICITY

CROSS-REFERENCE TO RELATED APPLICATIONS

The present application is a division of application Ser. No. 15/301,760 filed on Oct. 4, 2016, entitled, currently issued U.S. Pat. No. 9,901,618 B2, which is the national stage application, filed under 35 U.S.C. § 371, of International Patent Application No. PCT/IB2015/051640 filed on Mar. 6, 2015, which is incorporated by reference herein in its entirety.

FIELD OF THE ART

The present invention refers to the medical field. More in detail, the present invention refers to a new peptide system capable of blocking the NMDA-induced presynaptic release of glutamate. The present peptide system is adapted for being used for treating pathologies associated with glutamate excitotoxicity.

STATE OF THE ART

One of the most abundant amino acids in the brain is L-glutamate. Its most important function at the neuron level is the control of excitatory neurotransmission, which has been described since the 1950s and whose physiological antagonist is gamma-aminobutyric acid (GABA).

L-glutamate is considered to be the principal mediator of the excitatory signal and of the quick synaptic transmission in the central nervous system. L-glutamate plays a fundamental role in the development of the central nervous system (CNS), in the formation and elimination of the synapses, and in cell migration, differentiation and death. In addition, L-glutamate is an important molecule for the transmission of the signal also in peripheral organs and tissues, as well as in endocrine cells.

When it is freed at the physiological level, L-glutamate has a fundamental role in cerebral function and seems to be involved in many aspects of normal brain function, including cognition, memory and learning. Paradoxically, when L-glutamate reaches high levels in the synaptic space, it becomes highly toxic. It is therefore necessary to have an equilibrium of free L-glutamate as neurotransmitter and L-glutamate that has been removed and degraded from the synaptic space. If this equilibrium is well-controlled, it maintains the normal physiology of the synaptic transmission. When this equilibrium is, following some cause, imbalanced towards the persistence of L-glutamate in the synaptic space, this event leads to a toxic state that is very dangerous for cell survival. This pathological state is defined "glutamate excitotoxicity" and it exclusively regards the Central Nervous System (CNS) notwithstanding the ubiquitous nature of this amino acid.

The glutamatergic synaptic transmission occurs due to the presence of the L-glutamate receptors (GluRs) on the CNS cells. These receptors are divided into two main categories: ionotropic (iGluRs) and metabotropic (mGluRs) glutamatergic receptors.

These two receptor classes are distinguished for their functionality. Indeed, the ionotropic receptors are a set of proteins (subunits) which form an ionic channel on the cell membrane and transduce the signal by opening and flowing the ions outward and inward. Conversely, the metabotropic receptors are proteins that traverse the cell membrane, do not allow molecules to pass through the membrane but transfer the outside signal, starting a series of intracellular events (second messengers).

The subtypes NMDA, AMPA and kainate (KA) constitute part of the group of ionotropic receptors.

The group of metabotropic receptors is marked as mGluRs and 8 different proteins thereof are known.

Many studies have shown that the acute form of neurotoxicity from glutamate is mainly mediated by ionotropic receptors of glutamate (iGluRs). This form of neurotoxicity is characterized by an excessive activation of iGluRs presynaptic and post-synaptic, which involve the entrance within the neuron of great quantities of $Na^+$ which is passively followed by the $Cl^-$ ion and an outflow of $K^+$ ions. This movement of ions is responsible for the entrance of water, which causes neuronal "swelling", osmotic lysis and necrosis. In addition, a massive flow of $Ca^{2+}$ completes the ionic movement.

Among the glutamatergic receptors responsible for the presynaptic release of glutamate, there is that known as NMDA. This receptor was the first glutamatergic receptor discovered and characterized.

NMDA takes its name from the chemical substance that pharmacologically activates it in a specific manner, that is: N-Methyl D-Aspartate. It is a channel receptor activated by a ligand formed by 4 subunits which together create a pore in the cell membrane. Its localization in the neuron is both postsynaptic and presynaptic.

The NMDA channel has the particular characteristic of being normally blocked by the Magnesium ion. This "Magnesium block" does not occur when there is a depolarization of the neuron, for example when the other receptors of glutamate (AMPA, metabotropic) are activated.

The NMDA receptors are constituted by an assembly of multiple subunits: GLUN1 and GLUN2. The latter is in turn divided into other isoforms (2A-B-C-D). The composition in subunits is variable in the various parts of the brain and in the subcellular localization, but GLUN1 presence is required for normal receptor functionality.

The NMDA receptor complex has numerous different bond sites for different molecules that can modulate—since they are co-agonists together with glutamate—the opening of the channel and hence the intensities of the cellular response to this event. These modulator sites are that of glutamate (also site of NMDA), of glycine and of polyamines (spermine and spermidine).

Once the presynaptic NMDA channel is open, there is an entrance of $Na^+$, $Ca^{2+}$ ions and an exit of $K^+$ ions. This ionic movement leads to the depolarization of the membrane and hence to the liberation of glutamate. The depolarization by NMDA induces an increase and mobilization of intracellular $Ca^{2+}$ that activates all the systems that lead to the neurotransmitter liberation.

Even if many studies today have described the modes with which the NMDA receptor transfers the outside signal to the interior of the cell, much effort is still required in order to understand which are the proteins involved in this mechanism that binds the NMDA receptor and the liberation of glutamate.

The importance of this argument lies in the fact that many pathologies are associated with excitotoxicity and even if drugs exist for trying to oppose them, there is a pressing need to find new pharmacological targets that more specifically can be the target of innovative medicaments.

Glutamate, however, in addition to being essential for the life of neurons, can also become quite toxic. The excessive activation of GluRs during events of acute stress such as ischemia, cranial trauma and epileptic crises leads to the death of the cerebral neurons. In addition, the neurotoxicity of glutamate can also be involved in the pathogenesis of the various chronic diseases that are classified in the context of neurodegeneration and neuroinflammation. The neurotoxicity of glutamate can occur through an aberrant stimulation of the NMDA, AMPA, KA receptors or the group I of the metabotropic receptors of glutamate. The relative contribution of these different classes of receptors varies in accordance with the neurons involved and a variety of other circumstances.

Glutamate, by means of the excessive activation of such receptors, appears to carry out an important role in cellular death following various attacks, such as those associated with epileptic states, cerebral ischemia, perinatal asphyxia and cranial trauma. Still more specifically, it seems that the NMDA receptor is that which is more greatly involved in these pathologies; indeed, experimentally, by using NMDA antagonists it has been possible to reduce the size of the cerebral damage associated with these pathologies.

When the stress is severe, the cellular death occurs via necrosis, while if it is less severe, processes of apoptotic type may be triggered. The principal mechanism involved is the ionic imbalance connected to the excessive entrance of $Na^+$ and $Ca^{2+}$ through ligand-dependent and voltage-dependent channels. The increase of the intracellular $Ca^{2+}$ concentration activates, in a cascade manner, various enzymes that contribute to the death of the cells. There is a complex interaction between the changes of ionic homeostasis, altered energetic cell metabolism, toxicity of the mitochondria and oxidative stress from free radicals. It has also been proposed that the chronic activation of the GluRs receptors also plays a fundamental role, as this can induce processes of neurodegeneration in a variety of late-onset neurological disturbances. At least partially, the endogenous glutamate that excessively and chronically activates receptors like NMDA or AMPA appears to be the cause of the pathogenesis of diseases such as amyotrophic lateral sclerosis (ALS), multiple sclerosis, Huntington's disease, Alzheimer's disease and Parkinson's disease. Drugs for clinical use are on the market today, both for acute and chronic pathologies. Their activity is often that of NMDA receptor antagonist. This receptor block if on one hand appears effective and gives an initial benefic in some of these pathologies, on the other hand produces side effects that may even be severe. Medical research must therefore do its utmost to continue to identify the intracellular partners of the receptors, in this specific case NMDA, in a manner so as to render the action of possible drugs increasingly specific and less toxic.

The most common pathology that is the cause of a chronic dementia among the elderly population is Alzheimer's disease (AD).

In this pathology, the onset is progressive and develops from a young age, when the cognitive functions undergo a slight decline.

Then, after sporadic memory reduction episodes, there is an increase of the cognitive deficiencies both in language and in reality perception and in the capacity to perform normal daily activities.

It has by now been ascertained that the pathology is due to deposits of neuritic plaques and neurofibrillary tangles in the areas assigned to memory. These deposits, which lead over time to a progressive neuronal death, thus induce cerebral atrophy above all of the cortex and hippocampus.

It is recognized that fragments of beta-amyloid (Aβ) peptides, produced in excess by the amyloidogenic processing of the amyloid precursor protein (AβPP), are the first factor of the cause of AD.

Indeed, the extracellular accumulation of the Aβ peptides leads to the formation of the neuritic plaques. It is under discussion as to whether the species toxic for the neurons are the circulating extracellular peptides or the insoluble plaques.

The neurofibrillary tangles are another histopathological characteristic of the pathology. The protein most present in these tangles is the protein associated with the microtubules (Tau) in its hyperphosphorylated form. These intercellular aggregates are present in various neurodegenerative pathologies, which are called tauopathies. The hyperphosphorylation of this protein was indicated as the cause of the neuronal degeneration in these pathologies. Parkinson's disease (PD) is a neurodegenerative pathology in which specific areas of the central nervous system are damaged by mainly hitting the motor system with severe deambulation problems. This type of deficiency is attributed to the progressive degeneration of the dopaminergic neurons of the black substance that project to the striated body. At the molecular level in the cerebral tissue, PD is characterized by the accumulation of Lewy bodies, which are protein aggregates in which alpha-synuclein and ubiquitin can also be recognized among other elements. There are various genetic mutations and proteins that contribute to the pathology; among those presently known, there is also Parkin whose mutations are the cause of most of the family PD forms and the multifunctional protein DJ-1 which is involved in the transcription of various genes. The functional loss of DJ-1 is one of the causes of the early onset of PD.

Amyotrophic lateral sclerosis (ALS) is a highly-disabling degenerative neurological pathology that affects the cerebral motoneurons and the spinal cord.

The pathology starts with great exhaustion, which leads to muscular atrophy and progressively muscular paralysis is developed.

SLA is normally of sporadic origin but a percentage of hereditary forms is recognized. In the case of genetic forms, the mutation of the superoxide dismutase (SOD1) is the cause of the pathology. SOD1 is involved in the protection of neuronal cells from "oxidation" by playing a detoxifying role.

Mutated human SOD1 leads to the formation of aggregates which are toxic for the neuronal cells in question.

Huntington's disease (HD) is a neurodegenerative pathology with hereditary character, which falls within the category of pathologies from polyglutamine. The gradual atrophy of the striatal neurons is the main characteristic in this pathology, which leads to having very well known deambulation deficiencies.

HD is the result of the elongation in polyQ of the N-terminal chain of the Huntingtin protein (HTT), which is not degraded as such and is accumulated in the neurons.

Cerebral ischemia is not a pathology with degenerative character; however, hitting the nervous cells that are destined to die can have an important effect also in pathological co-morbidity with the other neurodegenerative pathologies, and it is present in epilepsies as well as in perinatal asphyxia and in cranial trauma. It is a highly-disabling disease which can be the cause of death or severe disabilities. The ischemia occurs in an apparently sudden manner when a cerebral area is no longer supplied by the normal blood flow due to a heart attack, aneurism, vasal occlusions, hemorrhages, traumas etc. The deprivation of oxygen and glucose during ischemia, and also the damage due to the blood reperfusion in the affected area lead the neuronal cells to undergo high metabolic stress.

At the cellular level, the ischemia causes a reduction of ATP, with increase of intracellular calcium, oxidative damage and mitochondrial dysfunctions. All these events lead to a high glutamatergic transmission, which results excitotoxic and hence damaging for the neuronal cells that are destined to die.

Multiple sclerosis (MS) is a demyelinizing chronic autoimmune disease, which hits the central nervous system, causing a wide range of signs and symptoms. Multiple sclerosis hits the nervous cells, rendering the communication between the brain and the spinal cord difficult. The nervous cells transmit electric signals through the axons, which are covered by an isolating substance, the myelin sheath. In the disease, the immune defenses of the patient attack and damage this sheath. When this occurs, the axons are no longer able to effectively transmit the signals. The pathogenetic mechanisms are complex and sustained by inflammatory and degeneratory processes on an excitotoxic basis; the exact etiology is still unknown. The different theories propose both genetic and infective causes; in addition, correlations with environmental risk factors have been indicated. The disease can manifest itself with a great array of neurological symptoms and can progress up to physical and cognitive disability. Multiple sclerosis can assume various forms, including relapsing and progressive forms.

Major depressive disorder is a mood disorder or pathology, characterized by episodes of depressed mood accompanied by low self-esteem and loss of interest or pleasure in normally enjoyable activities. Depression is a complex disease, due to genetic and environmental factors, which involves a complex network of neural systems. The most confirmed hypothesis is the "monoaminergic theory of depression", according to which the clinical depression would derive from a reduced efficiency of one or more types of cerebral synapses which use monoamines, such as serotonin, dopamine or noradrenaline. New studies have indicated the relation between depression and some variants of a group of genes involved in the transmission of glutamate signals. In accordance, it has been demonstrated that ketamine—a substance known for blocking the NMDA receptor—possesses antidepressive effects that are much quicker than those of conventional antidepressives, which instead require many weeks before showing results: ketamine is able to oppose depression in a much more effective manner than that which presently occurs with antidepressive drugs (which indeed do not effectively address the problem at present).

Schizophrenia is a severe mental disturbance, which is complex and often disabling. The first signs of schizophrenia are generally manifested during adolescence and in early adult years. The people affected by schizophrenia have difficulty in articulating their thoughts; this condition leads them to having hallucinations, deliria, incoherent thoughts as well as unusual behavior and speech. Due to these symptoms, the people hit by this disease have serious difficulties in interacting with others and tend to be isolated from the outside world. There have been various attempts to seek to explain the link between altered cerebral functionality and schizophrenia. One of the most classic hypotheses regards the role of dopamine: the malfunctioning of the dopaminergic neurons could be the cause of the symptoms that lead to the psychosis. Recent results support the hypothesis of the anomalous relation between the systems of the dopamine and glutamate neurotransmitters in physical subjects, and suggests that the development of drugs capable of affecting the glutamate transmission pathway may be useful in treating psychoses.

Anxiety disorders are a common form of mental disease which often cause significant anguish and problems and lead to a reduced quality of life. There are different types of anxiety disorders: for example, generalized anxiety disturbance, social anxiety disturbance, panic disturbance and obsessive-compulsive disturbance. The cause of anxiety disorders is unknown. Nevertheless, some alterations of the cerebral functions appear involved in various anxiety disorders. In addition, social and stress conditions could contribute to the development of anxiety disorders. The comprehension of the biological bases involved with fear, anxiety and correlated disturbances—even if still not fully complete—has seen considerable progress, due to the development of genetics, neurochemistry, psycopharmacology and neuroimaging techniques. In particular, a considerable increase regarding the knowledge of the neurobiological bases of anxiety is derived from the study of the behavioral components of the fear response, particularly related to the notions regarding the involved neuroanatomical pathways (amygdala, prefrontal cortex [PFC], thalamus and hippocampus), as well as the receptor and genetic aspects which can at least partly explain the different vulnerability of individuals to anxiety disorders. Among the neurotransmitters involved, an important role is played by GABA, glutamate, serotonin, neuropeptides and endocannabinoids.

Hemicrania is a highly-disabling neurological pathology limited to the central nervous system, which in the most severe cases is also associated with the symptoms of the autonomous nervous system. Typically the pathology is manifested with pain localized at the head, but is also associated with nausea, vomit, photophobia and phonophobia. Many of the people who suffer from hemicrania experience Aura, which is manifested in transitory visual, motor and sensory disturbances that precede cephalea. At present, the most confirmed molecular cause is the anomalous excitotoxic surge that occurs in the neurons, especially cortical, which is then followed by a depression of neuronal activity that is extended throughout the cortical area. The drugs presently used are the classic analgesic drugs associated with antiemetic drugs in the most severe cases. Hence, also in this pathology, the excessive release of glutamate is at the basis of the organ disturbances.

Another pathology in which the release of glutamate is one of the causes of the pain symptoms is chronic neuropathic pain. This is a pathology of the central nervous system that begins since the connection of the nervous signal between the peripheral fibers and the central fibers functions in an anomalous manner Generally, the symptoms are manifested with continuous burning sensations or electric shocks, and paresthesia are also often present around the zones of the primary pain location. Hyperalgesia and allodynia are a main characteristic of this pathology.

Neuropathic pain is unfortunately difficult to cure; the only drugs presently used are analgesic drugs, which often result ineffective.

The present invention is based on the identification of a very specific mechanism of glutamate release induced by the activation of the NMDA receptor localized on the presynaptic compartment of the neuronal terminations. In particular, the present invention, described in detail hereinbelow, attains the identification of the involvement of the protein c-Jun N-terminal Kinase (JNK) in the cascade of cellular events triggered by the activation of the NMDA receptor. This occurs while documenting—for the first time—the existence of the JNK proteins at the presynaptic level. Before embarking on a more detailed description, it is opportune to indicate that the JNKs are ubiquitous intracellular kinases with enzymatic activity associated with different signal pathways involved with many cellular functions. JNK are proteins that cover a central role in the signals that lead to neuronal death, which is verified in various pathological conditions. The JNKs can be activated following the stimulation of tyrosine kinase receptors, cytokine receptors, receptors coupled with G proteins and ligand-dependent ionic channels, including the NMDA receptor, and they represent a true indication for signaling cellular death. While JNK has been generally associated with the post-synaptic NMDA receptors, its presynaptic role remains largely undiscovered.

DESCRIPTION OF THE INVENTION

The present invention refers to a peptide system capable of specifically blocking the NMDA-induced presynaptic release of glutamate. In particular, the present invention refers to two cell-permeable peptides suitably prepared for inhibiting the interaction of proteins involved in the control of the glutamate release. Upstream of the definition of the present peptide system, by means of biochemical and electrophysiological methods the presence of JNK at the pre-synaptic level was demonstrated, involved in the control of the NMDA-evoked release of glutamate. In addition, by using knockout mice for the single isoforms of JNK in combination with molecular model studies, it was demonstrated, in the course of the studies pertaining to the present invention, that the isoform 2 of JNK is the essential protein that mediates this presynaptic event. More in detail, it was indicated that JNK2 lies in the presynaptic portion of the neuron and probably performs its action of control of the NMDA-mediated release by means of the interaction with an exclusively synaptic protein called Syntaxin 1a (STX 1a). Since STX 1a is an essential protein for the neurotransmitter release mechanism, the present invention is based on the study of the interaction between JNK2 and STX 1a, in order to define the portion where the two proteins interact. Two cell-permeable peptides have therefore been designed which are capable of blocking this JNK2-STX1a interaction. The peptides were designed in a manner such that they can pass the cellular barriers and inhibit the interaction that lies at the presynaptic level. These two peptides are thus capable of specifically blocking the NMDA-induced presynaptic release of glutamate. The two peptides will hereinbelow be termed JGRi1 and JGRi2.

A) shows the results of the glutamate release induced by NMDA stimulation in synaptosomes from the cortex of wild-type and JNK-KO mice pre-loaded with radioactive tracer. The results are expressed as a percentage of induced release. The data is the mean±SEM of 4 experiments conducted in triplicate (3 perfusion chambers for each experimental condition). p<0.01 vs. WT; p<0.05 vs. JNK1-KO or JNK3-KO. B) shows the representative Western blot results with quantifications that show the ratio pJNK/JNK in the JNK2-KO or JNK3-KO mice during the treatments. The results are expressed as percentages with respect to the control (100%). The data represents the mean±SEM of 3 experiments (p<0.01 vs. 100% of control).

Figure 5:
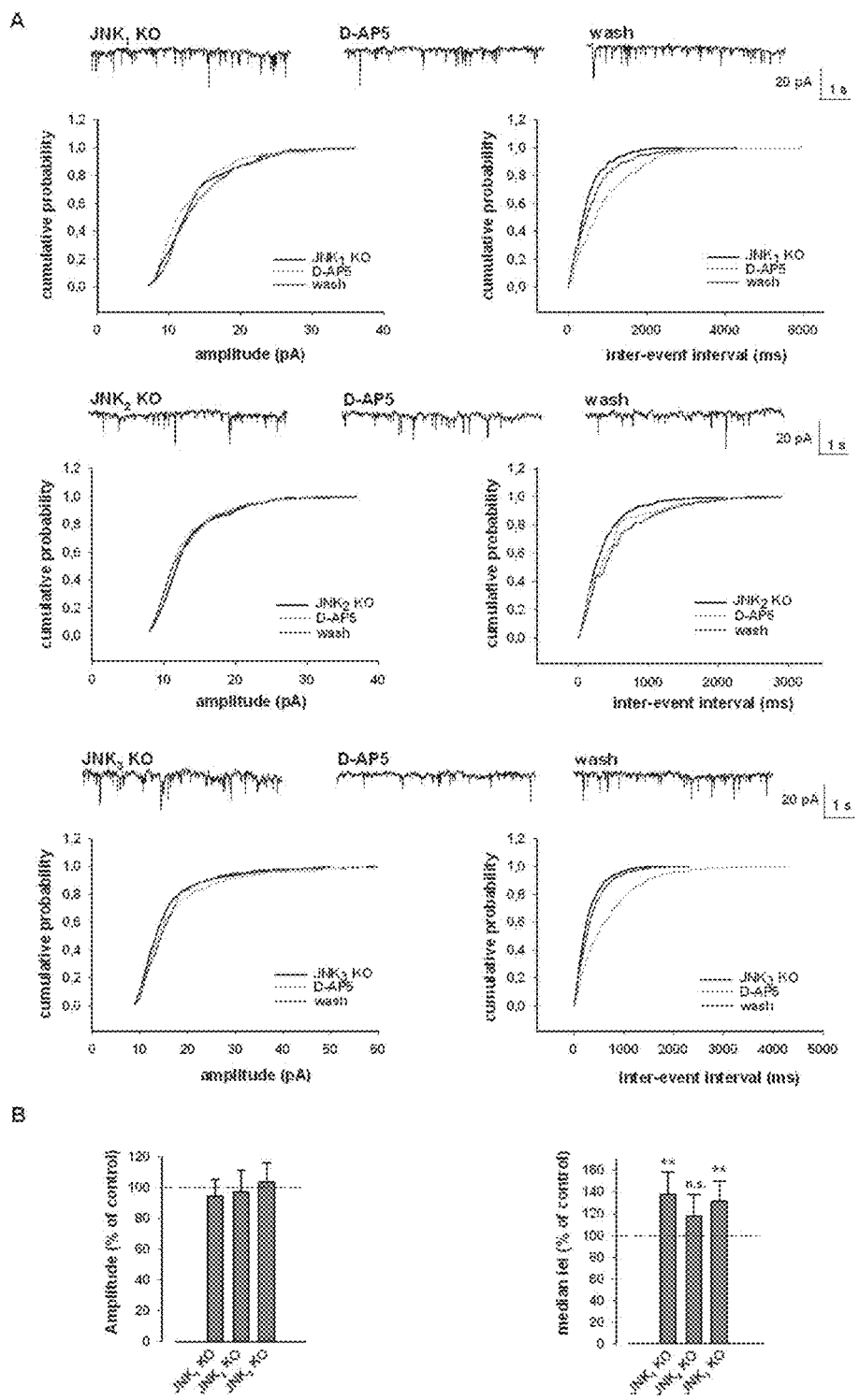

FIG. 5 shows how the isoform JNK2 is involved in the NMDA-mediated release of glutamate. A) represents the cumulative distribution of the amplitude of the mEPSC (left) and the inter-event intervals (right) recorded from single neurons of isoform JNK KO mice in response to D-AP5 (50 µM). The top lines are obtained from the same neurons, in control conditions, during the administration of D-AP5 and subsequent washing. B) represents the histograms (mean±S.E.M) of the means of the amplitude values of mEPSC (left) and inter-event intervals (right) with n=8 JNK1 KO, n=7 JNK2 KO and n=6 JNK3 KO neurons in response to the D-AP5. **p<0.01 t-test.

Figure 6:
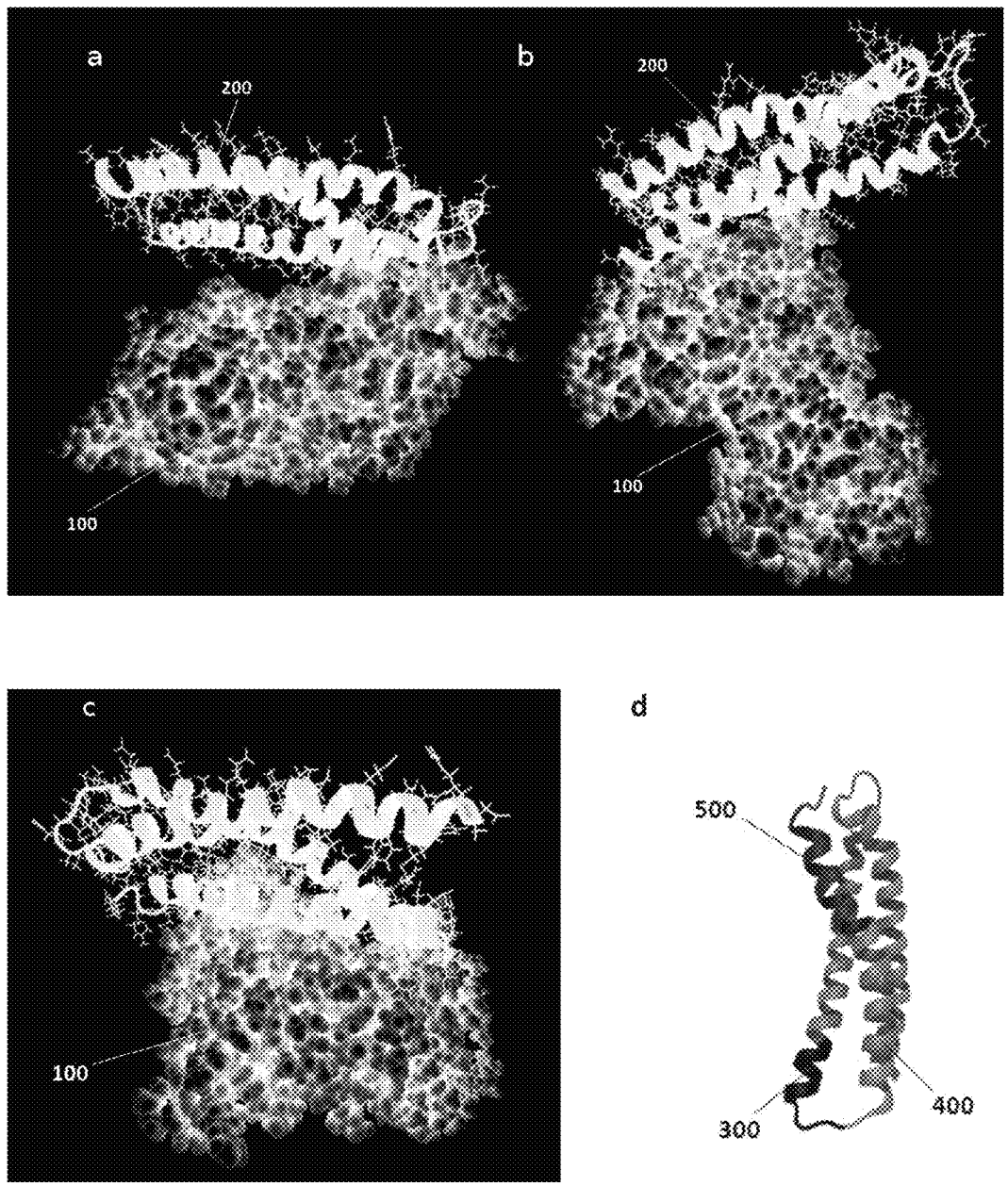

FIG. 6 shows the model of molecular docking of the protein interaction JNK-STX1a. A,B,C) represent the three best docking possibilities obtained from the study of the interaction between STX1a and JNK2 respectively identified as models 1, 2 and 3. The JNK2 protein is represented by the group 100, while the N-terminal portion of STX1a is represented by the group 200. D) shows the structure of the N-terminal portion of STX1a: the sections 300, 400, and 500 are shown which represent the portions that, with highest probability, interact with JNK2. The rendering of all the images was carried out by means of the use of VMD software.

Figure 7:
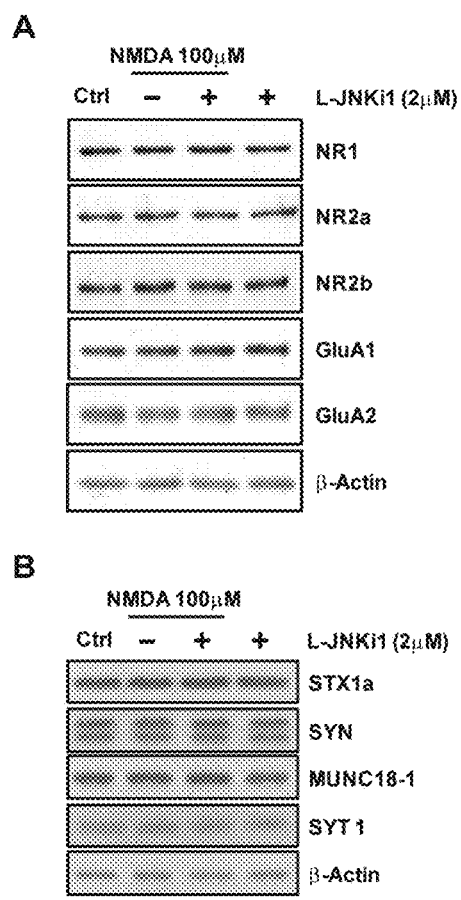

FIG. 7 shows that the treatment with L-JNKi1 does not induce changes in the NMDA and AMPA receptor subunits (A), nor does it induce changes on the proteins of the release mechanism (B), neither during NMDA stimulation conditions nor if applied on its own.

Figure 8:
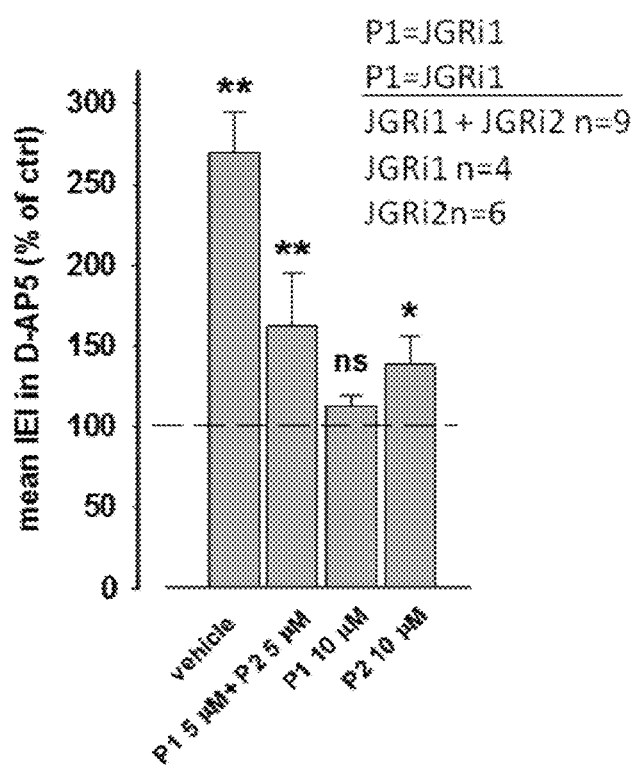

FIG. 8 shows the effect of the two peptides JGRi1 and JGRi2 on the release of glutamate in wild-type mouse cortex slices in electrophysiological patch-clamp experiments. More in detail, the figure in question shows the histograms (mean±S.E.M) of the means of the amplitude values of the inter-event intervals with n=9 neurons where JGRi1 and JGRi2 were applied together or n=4 neurons for JGRi1 and n=6 neurons for JGRi2. **p<0.01 t-test.

Figure 9:
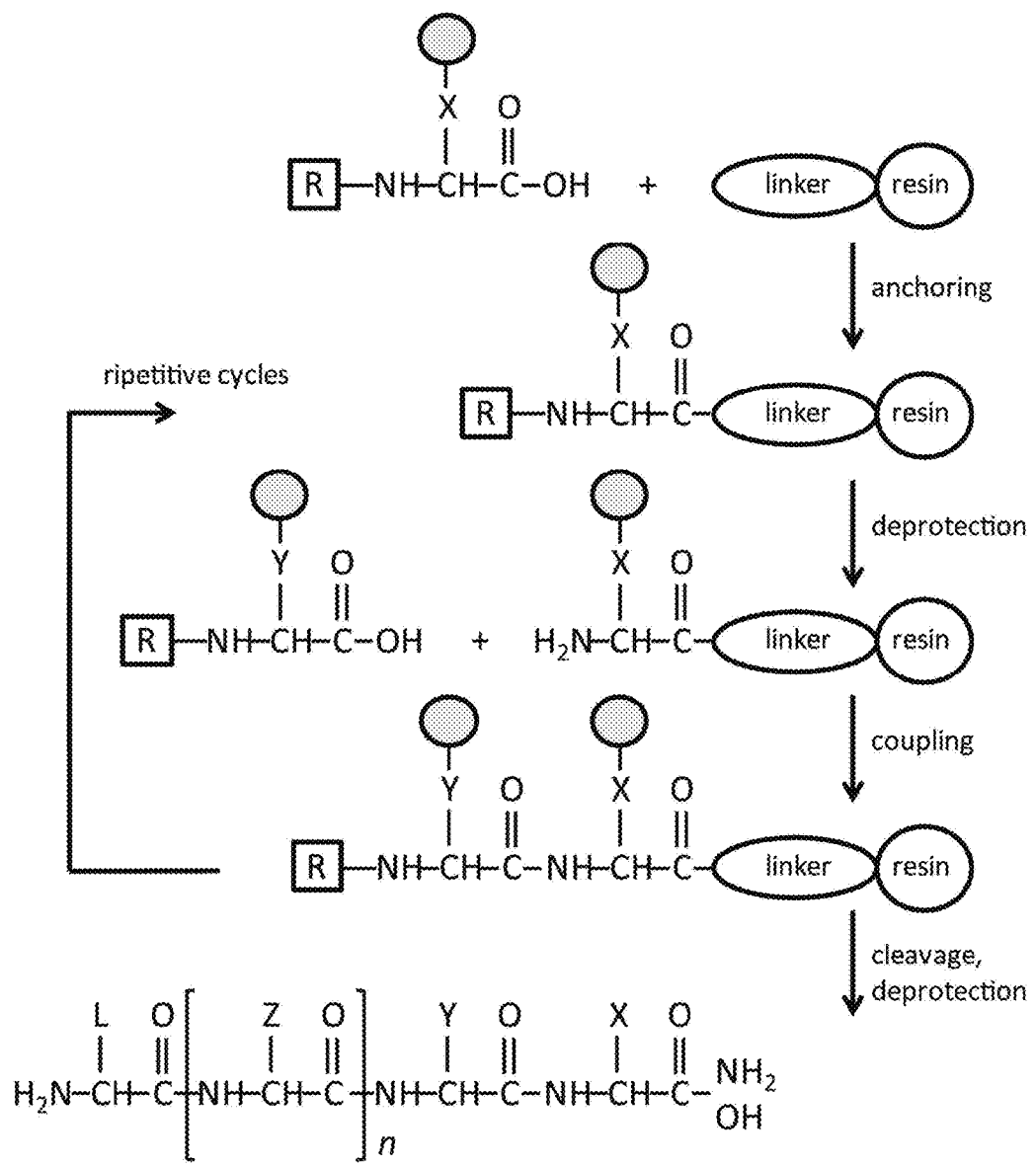

FIG. 9 shows an example of a solid-phase chemical synthesis process for peptides. The symbols indicate: little circle, group of protection for the amino acid chain; R, protection for the amino group; X, Y, Z, L, functional groups.

The process is cyclically repeated until the peptide is attained.

Figure 10:
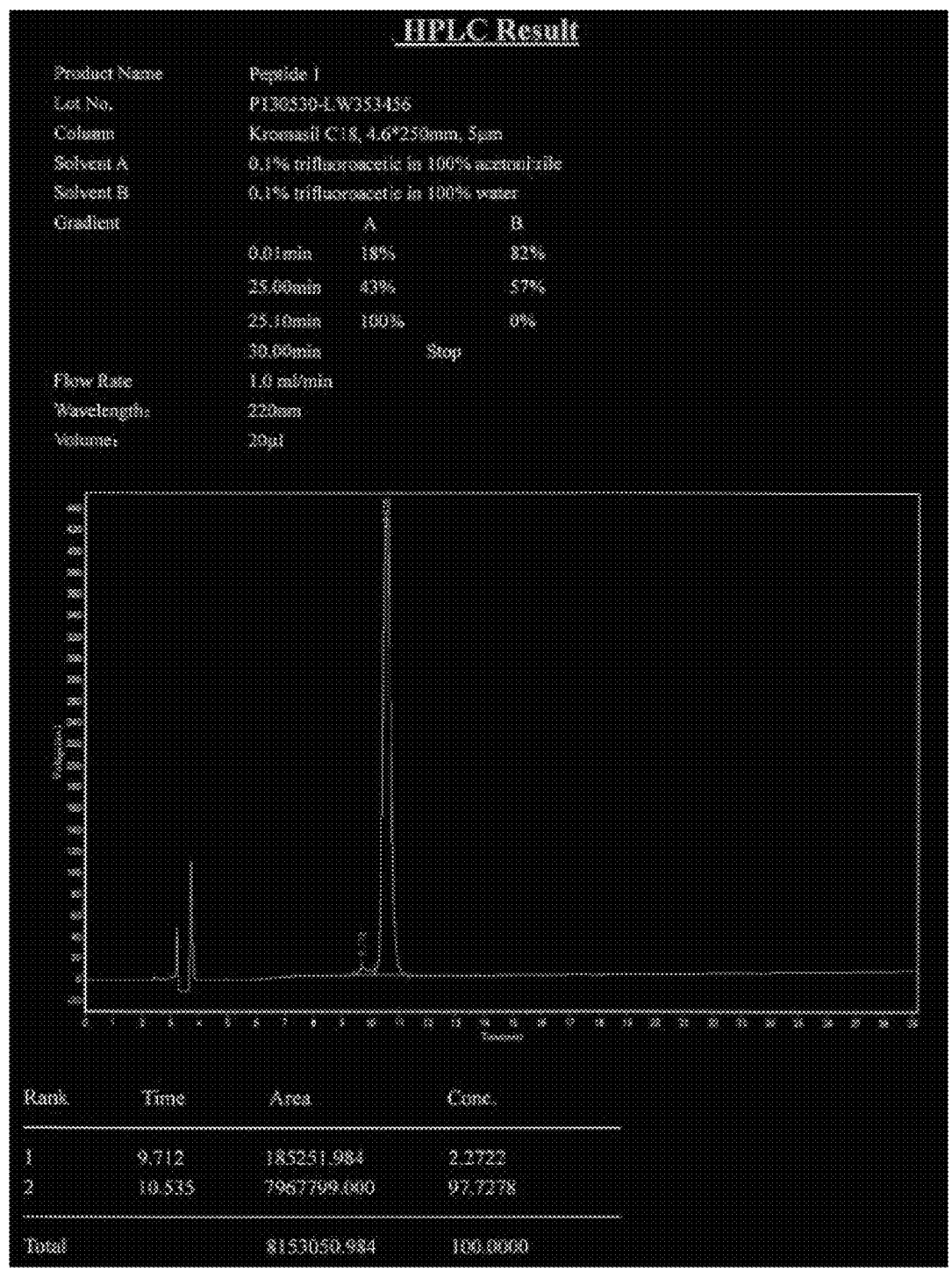

FIG. 10 shows the chromatogram obtained from the HPLC analysis of the peptide JGRi1 having sequence SEQ ID NO. 5: GRKKRRQRRRPPIEQSIEQEEGLNRS.

Figure 11:
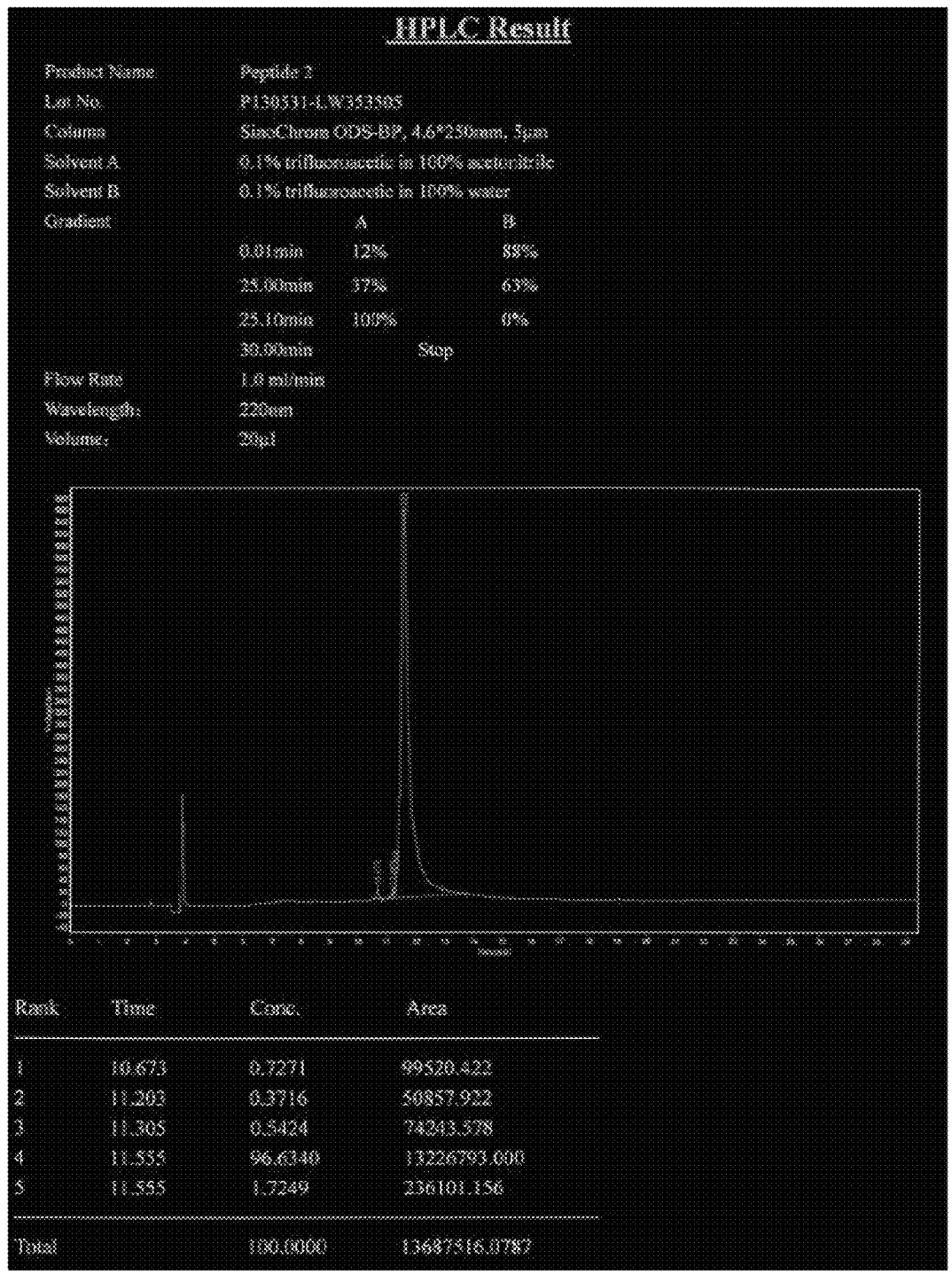

FIG. 11 shows the chromatogram obtained from the HPLC analysis of the peptide JGRi2 having sequence SEQ ID NO. 8: GRKKRRQRRRPPMSEYNATQSDYRER.

Figure 12:
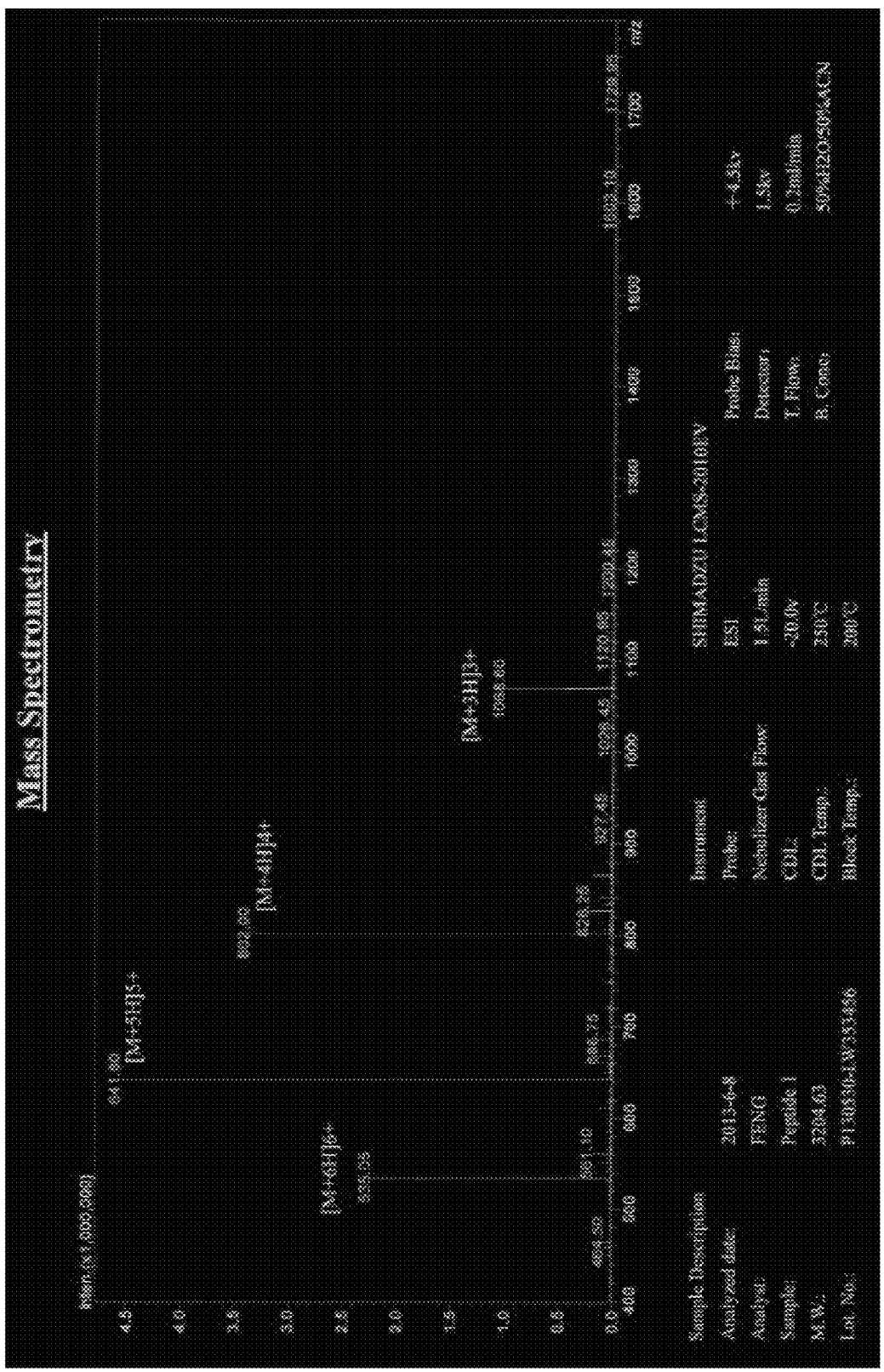

FIG. 12 shows the mass spectrum of the peptide JGRi1 having sequence SEQ ID NO. 5: GRKKRRQRRRP-PIEQSIEQEEGLNRS.

Figure 13:
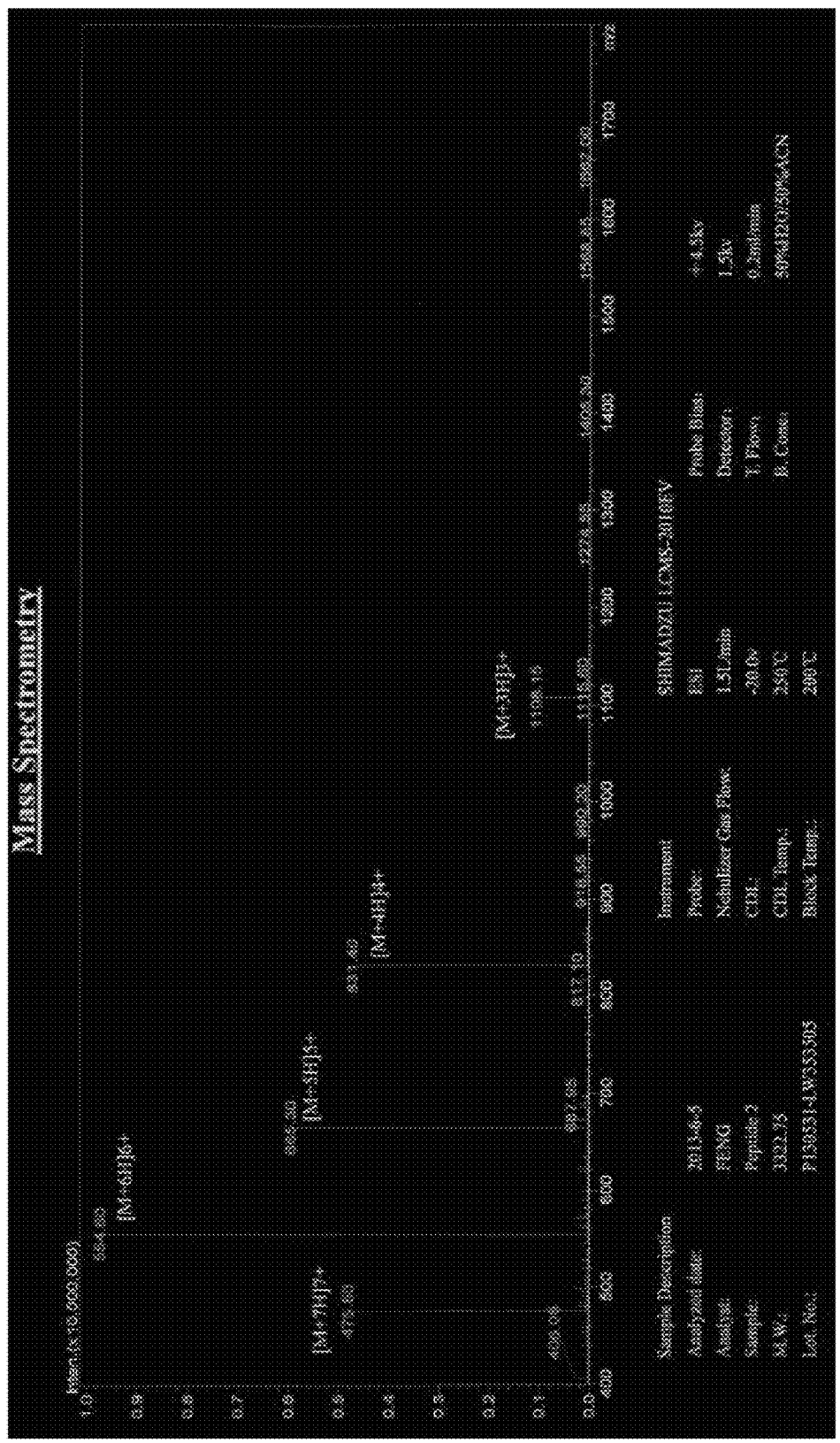

FIG. 13 shows the mass spectrum of the peptide JGRi2 having sequence SEQ ID NO. 8: GRKKRRQRRRPPM-SEYNATQSDYRER.

DETAILED DESCRIPTION OF THE INVENTION

The present invention is based on the demonstration of the presence of the JNK isoforms (JNK1, JNK2, JNK3) at the STX1a presynaptic level. Taking this protein interaction as the starting point, two peptides were designed: cell-permeable JGRi1 and JGRi2, which are capable of blocking this JNK2-STX1a interaction and reducing the release of glutamate induced by the stimulation of the NMDA receptor.

Figure 1:
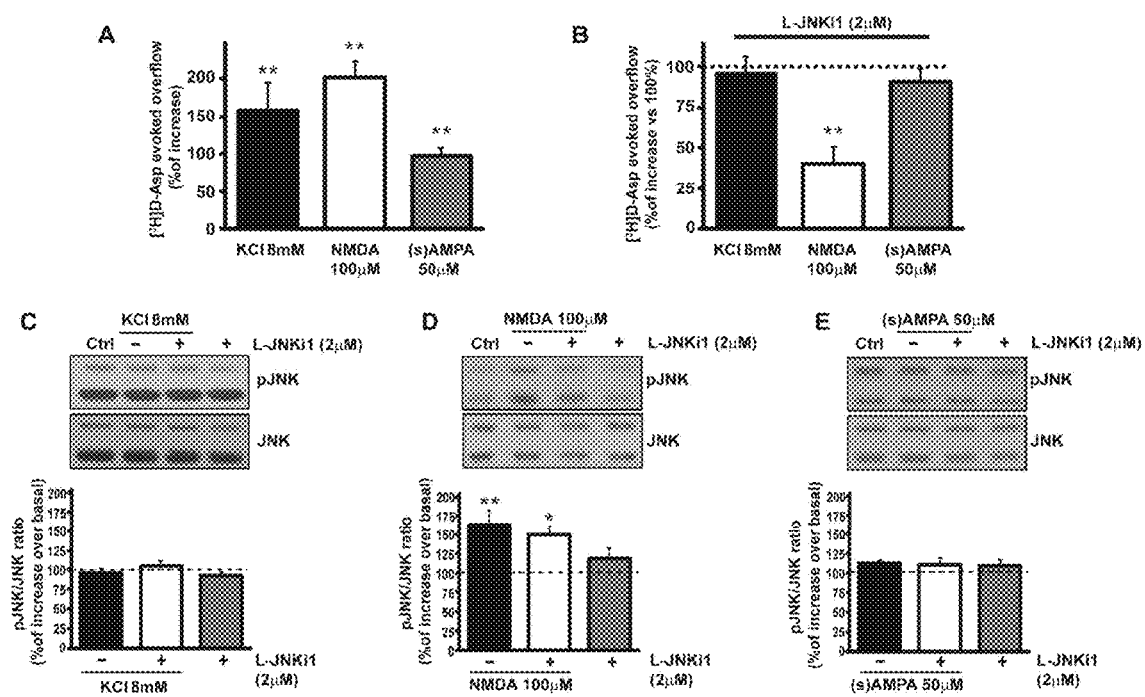
FIG. 1 shows the effect that the inhibition of the JNK protein has on the presynaptic release of glutamate, and it also shows the synaptic activation of the JNK protein under the action of different stimuli. A) shows the results regarding the synaptosomes prepared from the cortex of Wild-type mice, which were pre-loaded with the radioactive neurotransmitter and then incubated with different stimuli as indicated. The results are expressed as percentage of the induced release. The data is expressed as mean±SEM (standard error of the mean) obtained from 3 experiments reproduced in triplicate (Three perfusion chambers for each experimental condition). $p<0.01$ vs. basal release. B) Synaptosomes prepared from the cortex of Wild-type mice were pre-loaded with the radioactive neurotransmitter and incubated with L-JNKi1 (2 µM) for 30 min before the stimuli as indicated. The results are expressed as percentage of the induced release. The data is expressed as mean±SEM (standard error of the mean) obtained from 3 experiments reproduced in triplicate (Three perfusion chambers for each experimental condition). L-JNKi1 prevented the release evoked by the NMDA stimulation. $p<0.01$ vs. 100% of the release evoked by NMDA. C-D-E) representative Western blots with relative quantifications that show the p-JNK level reached after 90 sec of stimulation of KCl (C), 10 min of NMDA (D), 10 min of AMPA (E) and the treatment of the synaptosomes with L-JNKi1. The results are expressed as percentage of increase of the p-JNK/JNK ratio on the control (placed at 100%). The data represents the mean±SEM of 4 experiments for each condition. The treatment with NMDA induced an increase of the phosphorylation of JNK **$p<0.01$ vs. 100% of the control) while JNKi1 does not reduce the effect of the NMDA (*$p<0.05$ vs. 100% of the control).

Experimental Data c-Jun N-Terminal Kinase (JNK) Regulates the Presynaptic Release of Glutamate The physiological presence of JNK at the presynaptic level was demonstrated by executing the glutamate release experiments. Due to this experiment type, it was possible to study the role of the JNK kinases in the presynaptic compartment. Isolated cortical terminals (synaptosomes) of mouse strain C57/BL6 were used. These synaptosomes pre-loaded with tritiated D-aspartate ([$^3$H] D-Asp) were subjected to glutamate release induced by different stimuli. The synaptosomes were stimulated with a method that has been used for years, namely superfusion, in which the synaptosomes are continuously washed by a continuous current solution, and at a certain point they are stimulated. The tritiated glutamate that is liberated in this procedure is exclusively released due to presynaptic intracellular events and once collected is distributed into the beta-emitting radiation counters. The transient exposure of the synaptosomes (90 s) to a slight depolarization stimulation (8 mM KCl) induced a significant exocytotic release of [$^3$H] D-Asp (158±37% vs. control P<0.01), which is comparable to that obtained from 10 minutes of exposure to 100 µM NMDA (202±21% vs. control. p<0.01). The NMDA stimulation was applied in a medium lacking $Mg^{2+}$ in order to ensure the effectiveness of the presynaptic NMDA receptor. In the same manner, a stimulation of 10 min of 50 µM (S)-AMPA was capable of giving a significant increase of release of [$^3$H] D-Asp (98±11% vs. control. P<0.01) (FIG. 1A). All the applied stimuli are known for triggering the release of neurotransmitter in a $Ca^{2+}$-dependent manner. Then, in order to study possible presynaptic roles of JNK, a specific inhibitor (L-JNKi1) was used which blocks the JNK signaling cascade, preventing JNK interaction with the target proteins that bind the JNK binding domain (JBD). L-JNKi1 is a commercial cell-permeable peptide with which cortical synaptosomes were then treated for 30 minutes at 2 µM concentration. It is interesting to observe that only the release of NMDA—stimulated glutamate was strongly inhibited (−60±10% vs. control=100%. P<0.01) by the L-JNKi1 (FIG. 1B), indicating that there is a specificity of the JNK signaling cascade in the modulation exclusively of the NMDA-evoked release of glutamate.

The Activation of JNK at the Presynaptic Button Level

The above-reported results indicate for the first time the presence and hence the functionality of JNK in the presynaptic button. In addition, it is clear that the JNK are capable of regulating the release of glutamate induced by the activation of the NMDA receptor. In order to confirm the presynaptic position of the JNK and their possible activation, biochemical experiments were carried out on cortical synaptosomes of mice, measuring the phosphorylation induced by the above-listed stimuli (FIG. 1C-E). The phosphorylation of JNK was increased following 10 minutes of exposure to 100 μM NMDA in $Mg^{2+}$-free medium (+63±18% vs. control=100%. **P<0.01). Since L-JNKi1 does not affect the phosphorylation of JNK, even when it has been pre-incubated, the applied stimulus of NMDA continues to produce an increase of the phosphorylated JNK (+49±10% vs. control=100%. *P<0.05). Conversely, the JNK basal phosphorylation remained unchanged when L-JNKi1 was applied on its own, indicating that this substance has no effect in a basal system (FIG. 1D). The other two depolarizing stimuli, AMPA and KCl, are instead unable to increase the phosphorylation of JNK, indicating that it is the NMDA stimulus that specifically modulates the activity of JNK (FIG. 1C-E).

JNK Mediates the Presynaptic Release of NMDA-Dependent Glutamate

The presynaptic NMDA receptors on the glutamatergic terminals are activated by the spontaneously-released glutamate and, by means of a positive feedback mechanism, determine a tonic liberation of glutamate. Electrophysiological recordings were made in order to investigate the functional role of JNK in the release of glutamate. For this reason, a parameter termed paired-pulse facilitation (PPF) was measured from pyramidal neurons of cerebral slices of entorhinal cortex (EC)—obtained from adult mice C57BL6/J incubated with or without the inhibitor of JNK, L-JNKi1 (2 μM for 30 min). Such paired-pulse facilitation (PPF) is a paradigm studied by means of the electrophysiological recording technique in patch-clamp configuration.

Figure 2:
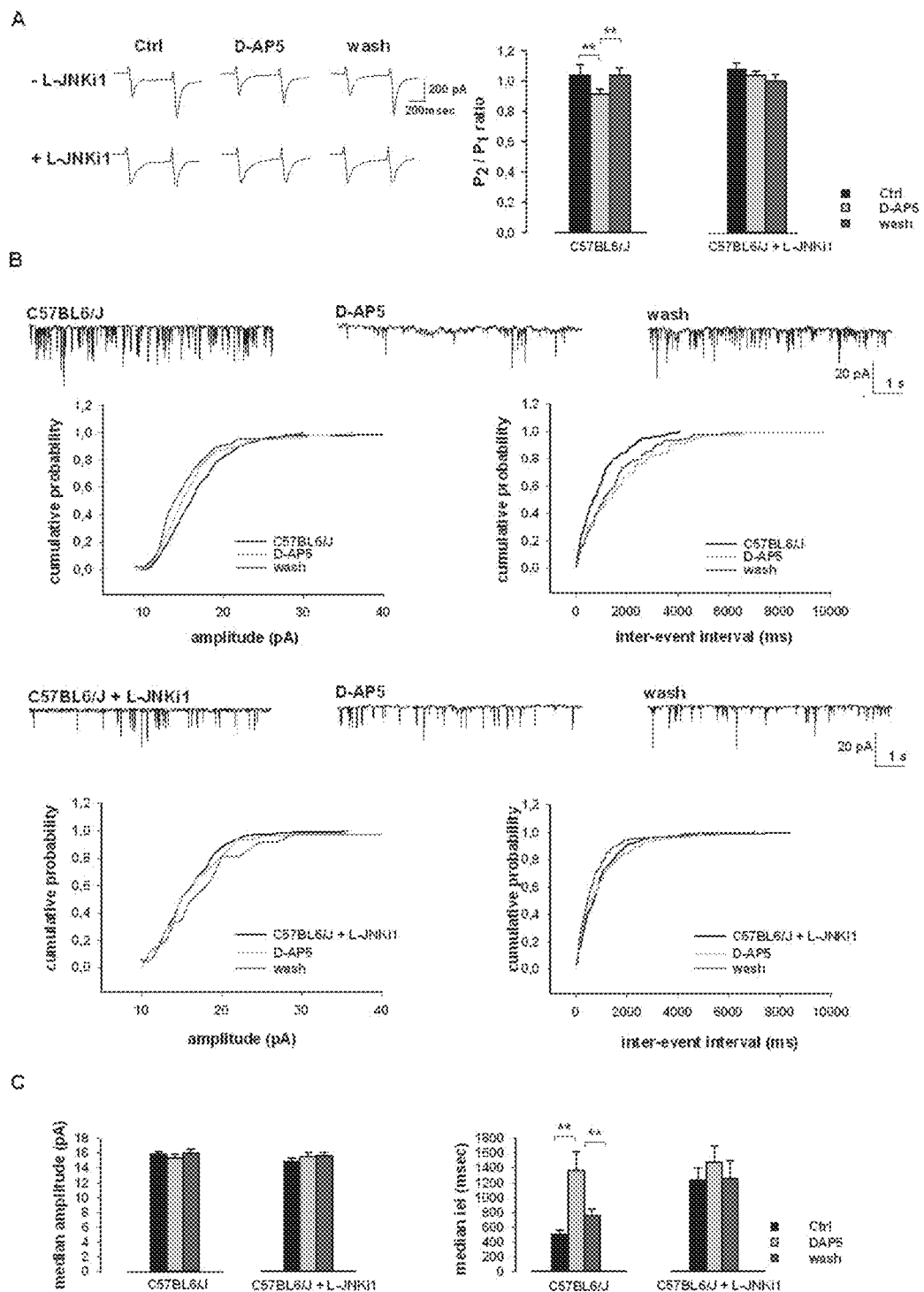
FIG. 2 shows the functional role of JNK in the release of glutamate dependent on NMDA. A) depicts the histograms (mean±S.E.M) of the paired-pulse ratio (PPR) of evoked EPSCs that are registered by 7 neurons from slices of mouse of the strain C57BL6/J and by 10 neurons of slices of mouse C57BL6/J pre-incubated with L-JNKi1 (2 µM). On the left, the representative traces were obtained from the same neurons, in control condition, during the administration of D-AP5 (50 µM) and after the washing of D-AP5. B) shows the cumulative distribution of the amplitude of the mEPSC (left) and of the inter-event intervals (right) recorded from single neurons of C57BL6/J, or of neurons of C57BL6/J pre-incubated with L-JNKi1 in response to the D-AP5. The top traces were obtained from the same neurons, in control conditions, during the administration of D-AP5 and subsequent washing. C) depicts the histograms (mean±S.E.M) of the paired-pulse ratio (PPR) of evoked EPSCs which are recorded from 11 neurons of slices of mouse of the strain C57BL6/J and from 10 neurons of slices of mouse C57BL6/J pre-incubated with L-JNKi1 (2 µM) in response to the D-AP5. **$p<0.01$ (t-test).

In this case, the perfusion with the antagonist of the NMDA receptor, D-AP5 (50 μM), irreversibly reduced the paired-pulse (PPR) relation obtained at 50 ms interval (p<0.01, Student t-test ctrl vs. D-AP5 n=7; p<0.01, Student t-test D-AP5 vs. washing n=7; FIG. 2A). When the slices were pre-incubated with L-JNKi1, the perfusion with D-AP5 did not change the PPR (p>0.05, Student t-test, ctrl vs. D-AP5, n=10; FIG. 2A). This data indicates that L-JNKi1 eliminates the probability of NMDA-dependent presynaptic release and is in line with the data of the release by synaptosomes, even in a more integral system like the cerebral slices.

Subsequently, the effect of L-JNKi1 was studied on the NMDA-dependent presynaptic glutamate release by measuring the excitatory currents of miniature type (mEPSCs), according to a protocol that is already commonly used. When the D-AP5 was applied in the presence of extracellular tetrodotoxin (1 mM) and picrotoxin (100 μM) together with MK-801 (10 mM), inhibitor of NMDA in the patch pipette (in order to block the postsynaptic NMDA channels in the cell being recorded), a reversible increase was seen of the distribution of the intervals between cumulative events (IEI) (*p<0.001, KS test, C57BL6/J vs. D-AP5, n=11; FIG. 2B) and of the mean values thereof (p<0.01, Student t-test, ctrl vs. D-AP5, n=11; FIG. 2C); in addition, neither the cumulative amplitude nor the mean of the same events were affected (p>0.05, KS test, C57BL6/J vs. D-AP5, n=11; FIG. 2B, p>0.05, Student t-test, ctrl vs. D-AP5, n=11; FIG. 2C). The reduction of the frequency by D-AP5 is due to the block of the presynaptic NMDA receptors, which facilitates the release of tonic glutamate. In slices pre-incubated with L-JNKi1, the D-AP5 effect is lost. Indeed, it was discovered that the perfusion with D-AP5 did not lead to significant changes of inter-event interval (p>0.05, KS test, C57BL6/J+L-JNKi1 vs. D-AP5, n=10; FIG. 2B; p>0.05, t-test of Student, ctrl vs. D-AP5, n=10; FIG. 2C), nor of the amplitude thereof (p>0.05, KS test, C57BL6/J+L-JNKi1 vs. D-AP5, n=10; FIG. 2B; p>0.05, Student t-test, ctrl vs. D-AP5, n=10; FIG. 2C). These results suggest that the inhibition of JNK reduces the release of glutamate mediated by the presynaptic NMDA receptors.

Overall, our electrophysiological data indicates that JNK performs a functional role in the NMDA-dependent release of glutamate in cerebral slices acutely treated with NMDA.

JNK Regulates the Phosphorylation of STX1a

Syntaxin 1a is an essential protein for the assembly of the SNARE complex (Soluble NSF Attachment Protein REceptor), which is an essential step for the release of neurotransmitter. The role of the phosphorylation of STX1a in ser14 (pSTX1a) in the neurotransmitter release mechanism is still a controversial subject. Some have reported that the reduction of pSTX1a has as direct consequence the diminution of the neurotransmitter release, while others demonstrated that the diminution of pSTX1a leads to facilitating the release of neurotransmitters.

Figure 3:
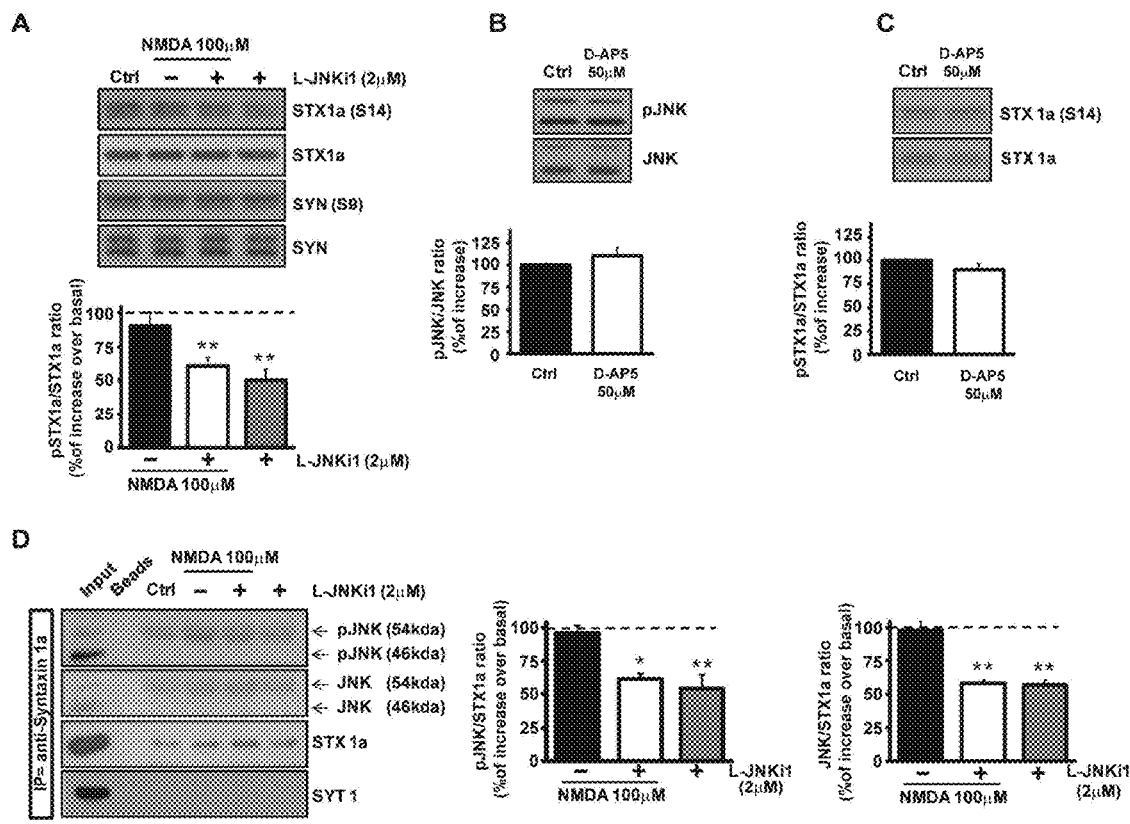
FIG. 3 shows that the JNK controls the phosphorylation of Syntaxin 1a and that JNK2/3 co-immunoprecipitates together with Syntaxin 1a. A) shows the representative Western blot results with respective quantifications of the phosphorylation of STX1a during the treatment as shown. The results are expressed as a percentage and are normalized with the control. The data is the mean±SEM of 5 experiments in which 10 min of NMDA+L-JNKi1 reduced the relation pSTX1a/STX1a ($p<0.01$ vs. 100% of the control) as did L-JNKi1 on its own ($p<0.01$ vs. 100% of the control). B) shows the representative Western blot results with the respective quantifications that show the levels of the phosphorylation of JNK during the treatment with D-AP5. The results are expressed as percentage with respect to the control (100%). The data is the mean±SEM of 3 experiments. C) shows the representative Western blot results with respective quantifications that show the levels of the phosphorylation of STX1a during the treatment with D-AP5. The results are expressed as percentage and are normalized with the control. The data represents the mean±SEM of 3 experiments. D) shows the results of the experiments of co-immunoprecipitation (Co-IP) with relative quantifications. Cortex synaptosomes of wild-type mice were stimulated as indicated in the figure and the immunoprecipitation executed with STX1a antibody. Representative Western blot results show Co-Ip of p-JNK and JNK after stripping procedure. The membranes were blotted for STX1a (as control of the immunoprecipitation) and for SYT1 (as control of the specificity). The results are expressed as percentage of increase of the relation p-JNK/STX1a or JNK/STX1a with respect to the control condition. The data is the mean±SEM of 4 experiments for each treatment (*p<0.05, **p<0.01 vs. 100% of the control).

Following an exposure of NMDA for 10 min, there is an increase of the JNK phosphorylation (FIG. 1D), which causes a slight but non-significant decrease in the phosphorylation of STX1a (STX1a (S14)) (FIG. 3A). It is interesting to observe that a pre-treatment with L-JNKi1 for 30 minutes followed by a stimulation of NMDA causes a significant reduction of pSTX1a (−40±6.4% vs. control=100%. P<0.01). The administration of L-JNKi1 on its own, even if it had no effect on the phosphorylation of JNK (FIG. 1D), surprisingly causes a strong reduction of the phosphorylation of STX1a (−45±6.4% vs. control=100%. P<0.01). In order to explain this phenomenon, we can assume that, since the synaptosomes are held in batches with a medium lacking $Mg^{2+}$, the neurotransmitters, including glutamate, could be accumulated in the extracellular compartment, and are thus able to activate the receptors even when L-JNKi1 is applied on its own. The NMDA antagonist D-AP5 was then applied for estimating possible changes in the pJNK (+10±8.9% vs. Ctrl) (FIG. 3B) or pSTX1a (−10±7.2% vs. Ctrl) (FIG. 3C) with respect to the control conditions (100%), therefore excluding the possibility that such changes occurred. Since other proteins are known to be part of the neurotransmitter release system, the possible interaction of JNK with the phosphorylation of synapsin was analyzed.

The phosphorylation of synapsin (SYN (S9)) was not affected by the stimuli caused in all experimental conditions (FIG. 3A). Overall, these results allow us to assume that the inhibition of the JNK activity specifically reduces the phosphorylation of STX1a.

JNK Interacts with STX1a

In order to better understand the synergistic interaction between JNK and STX1a in the NMDA-induced release of glutamate, co-immunoprecipitation (Co-IP) experiments were conducted (FIG. 3D). The proteins extracted from the synaptosomes were immunoprecipitated with an antibody specific for STX1a and then by means of Western blot pJNK and JNK were detected with specific antibodies. The control (non-immunoprecipitated sample) gave the typical JNK signal with a lower band (JNK1, 46 kDa) and an upper band (JNK2/3, 54 kDa). Surprisingly, STX1a immunoprecipitates only the JNK 2 and 3 isoforms, both as JNK and in the phosphorylated pJNK form; indeed, the antibody detected the upper band. This result clearly prevents the protein STX1a from bonding to JNK1, and suggests that the formation of the STX1a and JNK2/3 interaction is already verified in basal conditions (Ctrl). In addition, both the immunoreactivity of JNK and pJNK were strongly reduced with respect to control conditions when L-JNKi1 was applied with NMDA (fig. ratio 3D JNK/STX1a:−42±2% vs. control=100%; **p<0.01 and ratio pJNK/STX1a:−39±3% vs. control=100%; *p<0.05), suggesting that the protein-protein interaction is perturbed by L-JNKi1. It is interesting to observe that the STX1a-JNK2/3 interaction was reduced in non-stimulated conditions by applying L-JNKi1 (FIG. 3D JNK/STX1a:−44±4% vs. control=100%; p<0.01 and ratio pJNK/STX1a:−46±8% vs. control=100%; p<0.01), showing that the interaction is constitutively present. In order to evaluate the specificity of the immunoprecipitate, the anti-synaptotagmin 1 antibody (Syt1) was also used, which is not immunoprecipitated, indicating that the interaction STX1a-JNK2/3 is specific.

Figure 4:
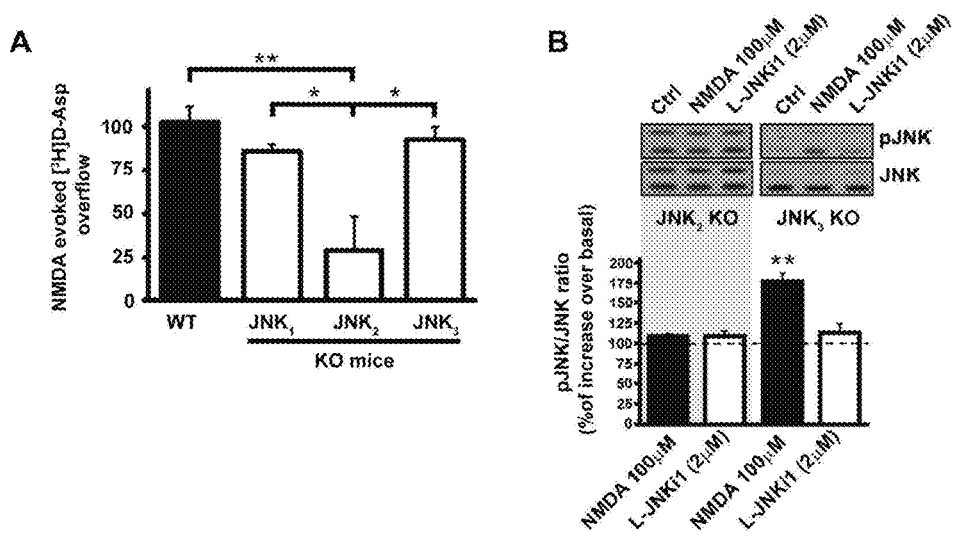
FIG. 4 shows how the NMDA-evoked release of glutamate and the NMDA-induced phosphorylation of JNK are inhibited in the JNK2 KO mice.

In JNK2 Knock-Out Mice, the Release of Glutamate and the Phosphorylation of JNK are No Longer Induced by NMDA In order to identify the specific isoform of JNK that is activated by the NMDA stimulation in the presynaptic compartment, glutamate release experiments were conducted on cortical synaptosomes obtained from JNK knock-out (KO) mice. The release of glutamate, measured as outflow of [$^3$H] D-Asp, was induced by NMDA applied for 10 min. It is interesting to observe that NMDA induces a release that is significantly lower, with respect to the basal (28±19% with respect to the overflow basal), only in JNK2-KO mice with respect to JNK1, JNK3-KO mice and wild-type mice (WT) (FIG. 4A). This result suggests that the presynaptic JNK2 isoform in particular controls the NMDA—evoked release.

In order to confirm the release experiments, it was studied, on synaptosomes stimulated with NMDA, if the absence of JNK2 reduced the phosphorylation of JNK. As expected, in the JNK2-KO mice the phosphorylation of JNK was totally eliminated with respect to the control. Conversely, it is still maintained in the JNK3-KO mice where NMDA induces an increase of pJNK (+76±10% with respect to the control=100%; **p<0.01) (FIG. 4B) fully comparable with that obtained in WT mice (FIG. 1D). In both cases, L-JNKi1 on its own is not able to affect the phosphorylation of JNK.

JNK2 Modulates the NMDA-Dependent Release of Glutamate in Patch-Clamp Experiments Electrophysiological recordings were carried out by recording the mEPSC, using the same above-described protocol from JNK1 KO, JNK2-KO and JNK3-KO mice. The perfusion of D-AP5 induces an increase of the cumulative distribution of the inter-event intervals in JNK1-KO (*p<0.001, KS test, JNK1 KO vs. D-AP5, FIG. 5A) and JNK3 KO (*p<0.001, KS test, JNK3-KO vs. D-AP5, FIG. 5A) and an increase of the mean values (**p<0.01, Student t-test, control vs. JNK1 or JNK3 KO; FIG. 5B). In both genotypes, the amplitude of the mEPSC was never affected by D-AP5 (p>0.05, KS test, JNK1 or JNK3-KO vs. D-AP5, FIG. 5A; P>0.05, Student t-test, control vs. JNK1 or JNK3 KO; FIG. 5B), while the diminution of the glutamate release due to the application of D-AP5 has been specifically reduced in JNK2-KO mice. Indeed, D-AP5 produced no significant changes in mEPSC (p>0.05, KS test, JNK2-KO vs. D-P5; FIG. 5A; p>0.05, Student t-test, control vs. JNK2 KO, FIG. 5B), or in amplitude (p>0.05, KS test, JNK2-KO vs. D-P5, FIG. 5A; p>0.05, Student t-test, control vs. JNK2 KO, FIG. 5B). Overall, this data suggests that only the JNK2 isoform mediates the presynaptic release of glutamate in our experimental conditions.

Docking Results for the JNK Variants

By comparing the different sequences of the three JNK, it was observed that JNK1 provides 18 characteristic residues, JNK2 45, while JNK3 only 11. Characteristic residues are defined as those residues that are specific variants of only one isoform, being differentiated with respect to the other two JNK.

The characteristic residues are important in the protein-protein interactions, and specifically if Syntaxin 1a specifically interacts with only one variant of JNK, the characteristic residues of such variant should be different with respect to the other JNKs. The fact that JNK2 is significantly different from JNK1 and JNK3 could be a first indication of its specific interaction with Syntaxin.

Subsequently, simulations of protein-protein docking were executed for modeling the complex between Syntaxin 1a and JNK2 using the Rosetta software.

It was observed that the three main structures deriving from the analysis are the three best-classified structures based on the interface score. A rendering image of each of these is reported in FIG. 6, in which JNK2 is represented by the group 100 and the N-terminal of Syntaxin 1a by the group (200).

In order to better evaluate these structures, the hidden surface areas were calculated. In models 1 (FIG. 6a) and 2 (FIG. 6b), there is a hidden surface area of about 1700 A2, while model 3 (FIG. 6c) presents a surface area of 2680 A2. The interface residues were then analyzed and compared with the characteristic residues of JNK2. This test demonstrated that in model 3, the N-terminal of Syntaxin 1a interacts with eight characteristic residues, in model 2 with five such residues and in model 1 with only two such residues. These observations led us to interpret model 3 as the best interaction conformation obtained.

A rendering image was then obtained that indicates the possible contact sites of the N-terminal portion of Syntaxin 1a (sections 300 and 400).

The Inhibition of JNK does not Induce Changes in the Machinery of the Vesicular Proteins and of the Subunit Levels of the NMDA or AMPA Receptor.

The expression levels were then monitored of several presynaptic proteins such as Syntaxin 1a (STX1a), synapsin (SYN), Munc18-1 and synaptotagmin 1 (Syt1), since their alteration compromises the release mechanism of the neurotransmitter. In our experimental conditions, L-JNKi1, if applied on its own or in combination with NMDA, did not modify the presence of STX1a, SYN, Munc18-1 and Syt1 in synaptosomes (FIG. 7A). In the same manner, the expression of the subunits of the NMDA and AMPA receptor (FIG. 7B) remained unchanged, thus ensuring that the NMDA-mediated effect on presynaptic JNK does not depend on specific modifications of their expression levels.

Analysis and Construction of the Peptides Inhibiting the Release of Glutamate

Analyzing the amino acid sequence of the N-terminal portion of Syntaxin 1a, 3 different residues can be identified which form the characteristic 3 alpha-helices; these are Ha, Hb and Hc. Hereinbelow, the amino acid sequence is shown (288 amino acids total):

SEQ ID NO. 1:
MKDRTQELRTAKDSDDDDDVTVTVDRDR(28)FMDEFFEQVEEIRGFID

KIAENVEEVKRKHSAIL(62)ASPNPDEKT(71)KEELEELMSDIKKTA

NKVRSKLKSIEQSIEQEE(104)GLNRSSA(111)DLRIRKTQHSTLSR

KFVEVMSEYNATQSDYRER(144)CKGRIQRQLEITGRTTTSEELEDML

ESGNPAIFASGIIMDSSISKQALSEIETRHSEIIKLETSIRELHDMFMD

MAMLVESQGEMIDRIEYNVEHAVDYVERAVSDTKKAVKYQSKARRKKIM

IIICCVILGIIASTIGGIFG

Ha goes from amino acid 28 to 62
Hb goes from amino acid 71 to 104
Hc goes from amino acid 111 to 144
The two sequences that have been identified as point of interaction of JNK2 on Syntaxin 1a are the following:

1)
SEQ ID NO. 2:
IEQEEGLNRS

2)
SEQ ID NO. 3:
MSEYNATQSDYRER

These two sequences were then taken under consideration for the construction of two cell-permeable peptides JGRi1 and JGRi2.

The functionality of the peptides is based on the principle of interruption of the interaction of the JNK2 protein with the N-terminal portion of Syntaxin 1a. Hence, if the cell is provided with an amino acid sequence of Syntaxin 1a of different length, that varies from the sites of minimum interaction between the two proteins or up to the entire portion of the N-terminal of Syntaxin 1a, these peptides will competitively participate in the interaction with JNK2, thus inhibiting the bond with endogenous Syntaxin 1a. This event is capable of reducing the release of glutamate. The peptides that can be considered effective vary in length starting from the entire N-terminal portion of Syntaxin 1a, 288 amino acids, to a minimum of 10 amino acids corresponding to the sequence SEQ ID NO. 2: IEQEEGLNRS or of 14 amino acids corresponding to the sequence SEQ ID NO. 3: MSEYNATQSDYRER.

In order to render the peptides cell-permeable, the sequence of the Tat protein (48-59) of the HIV virus was inserted before the N-terminal portion of the present sequences, hence adding another 12 amino acids.

Tat (48-59) has the following sequence of 12 amino acids: GRKKRRQRRRPP.

This sequence is very effective, whether it is added in N- or C-terminal position of each of the possible synthesized peptides. One example of peptides are those synthesized in a manner so as to have a total length of 26 amino acids.

The sequences of the two peptides are the following:
JGRi1 (SEQ ID NO. 5): GRKKRRQRRRP-PIEQSIEQEEGLNRS
or (SEQ ID NO. 6) IEQSIEQEEGLNRSGRKKRRQR-RRPP or even the respective mirrored sequences with regard to the tat sequence
e.g. (SEQ ID NO. 7) PPRRRQRRKKRGIEQSIEQEEGL-NRS
JGRi2 (SEQ ID NO. 8): GRKKRRQRRRPPMSEYNATQS-DYRER
or (SEQ ID NO. 9) MSEYNATQSDYRERGRKKRRQR-RRPP or even the respective mirrored sequences with regard to the tat sequence e.g. (SEQ ID NO. 10) PPRRRQRRKKRGMSEYNATQS-DYRER The two peptides were synthesized with amino acids having L enantiomer structure, but also synthesized as D enantiomers in order to improve the stability thereof in a living organism.

The same sequences can be inserted, as corresponding DNA sequences, also in different vectors for expressions in cell lines, bacteria and also in vectors for virus production.

The insertion in the expression vectors can be of whole sequences, and hence as
JGRi1 (SEQ ID NO. 5): GRKKRRQRRRP-PIEQSIEQEEGLNRS
or (SEQ ID NO. 6) IEQSIEQEEGLNRSGRKKRRQR-RRPP or also the respective mirrored sequences with regard to the tat sequence.

For example (SEQ ID NO. 7) PPRRRQRRK-KRGIEQSIEQEEGLNRS JGRi2 (SEQ ID NO. 8): GRK-KRRQRRRPPMSEYNATQSDYRER or (SEQ ID NO. 9) MSEYNATQSDYRERGRKKRRQRRRPP or also the respective mirrored sequences with regard to the tat sequence e.g. (SEQ ID NO. 5) PPRRRQRRKKRGM-SEYNATQSDYRER or by adding the different domains, hence first the sequence of TAT and then that (SEQ ID NO. 2) IEQEEGLNRS or (SEQ ID NO. 3) MSEYNATQS-DYRER or vice versa. In addition, in order to render the final protein recognizable in cellular systems, small pieces of DNA may be added which encode small (tag) peptides, such as HA, GST, Myc, EGFP etc.

For example: pGEX-4, pTAT, p-EGFP-C1, pc-DNA, 3 generation lentiviral vectors, commercial or not also used for gene therapy, vectors for Sindbis virus, adenovirus for infection (transduction) of neurons.

The two peptides were tested in glutamate release experiments (as described above) and in electrophysiology experiments (patch clamp, as described above) in order to test their effectiveness in reducing the NMD-evoked release of neurotransmitter.

Both peptides resulted active in decreasing the NMDA-dependent release of glutamate in patch-clamp experiments. Mouse cortex slices were treated for 30 minutes before the recording of the cumulative distribution of the inter-events of the mEPSC with the peptides in various condition. The two peptides (JGRi1 and JGRi2), whether added together at the concentration of 5 μM or separately at the concentration of 10 μM, reduced the functionality of the inhibitor D-AP5 in blocking the NMDA presynaptic receptor (FIG. 8). This data indicates that the NMDA receptor is already effectively blocked by the two peptides in the intracellular pathway and hence the receptor inhibitor, which acts on the extracellular portion of NMDA, no longer has effect.

The two peptides demonstrated effectiveness both on the synaptosomes and on cerebral slices, indicating that, given that they were administered in the extracellular environment, they are capable of penetrating into the cells, also diffusing into integral tissue. It is also expected that the peptides are capable of being entirely diffused in an organism. In order to reduce their degradation, and hence increase their hemi-life, the present peptide system was synthesized by using amino acids belonging to the D stereochemical series.

D-JGRi1: dG-dR-dK-dK-dR-dR-dQ-dR-dR-dR-dP-dP-dI-dE-dQ-dS-dI-dE-dQ-dE-dE-dG-dL-dN-dR-dS
D-JGRi2: d-G-dR-dK-dK-dR-dR-dQ-dR-dR-dR-dP-dP-dM-dS-dE-dY-dN-dA-dT-dQ-dS-dD-dY-dR-dE-dR.

The possible administration routes of these cell-permeable peptides comprise all the known combinations, which range from those with immediate bioavailability to those with release modified over time.

We include in the administration modes those via intraperitoneal, intramuscular, subcutaneous and intravenous injection (physiological solutions of the peptide system), transdermal absorption pathways (plaster, ointments, creams, oils, etc.), sublingual (pasty or solid solutions), intranasal (various physiological solutions) and oral (oral preparations such as suspensions, tablets, capsules, etc.) routes.

In addition, all the nanotechnological formulations that produce a modified release, whether transdermal or systemic via injection or oral administration.

In addition, a new administration route is considered: the production of neuronal stem cells, engineered such that they produce the peptide system in cell-permeable form (expressing the sequence Tat) or non-cell-permeable form. These cells, once injected and once they have reached the cerebral zone hit by degenerative pathology, can proliferate and liberate the peptide system in situ.

Process of Preparing the Present Peptide System

The synthesis of these peptides was carried out by means of chemical practice often used today, which allows obtaining amino acid chains up to even 70 residues. A solid-phase chemical synthesizer was used in which the first amino acid is anchored to a solid base (resin) and then by means of isopeptide reactions between the amino acids, the chain of the peptide is elongated via repeated cycles (FIG. 9; modified by Current Protocols in Molecular Biology (2002) 11.15.1-11.15.9).

After synthesis, an HPLC (High Performance Liquid Chromatography) analysis is used for purifying the peptide from contaminants, which is the reaction waste. In addition, a cycle of Mass spectrometry is carried out in order to verify the identity of the peptide. The peptides are considered good when the obtained yield (with regard to the peptides with 26 amino acids) exceeds 95%.

The peptide chain is formed using amino acids in L stereochemical form, if the final peptide is in L form, as well as those in D form, if the final peptide is in D form.

Plasmid Vector Synthesis.

With regard to the plasmid systems, the nucleotide sequence of the peptides—whether they all comprise the N-terminal portion of Syntaxin 1a or even smaller peptides up to a length of 10 amino acids corresponding to the sequence (SEQ ID NO. 2) IEQEEGLNRS and of 14 amino acids corresponding to the sequence (SEQ ID NO. 3) MSEYNATQSDYRER and for all possible lengths, also with the addition at the front (N-terminal) or at the back (C-terminal) of the sequence Tat=(SEQ ID NO. 4) GRK-KRRQRRRPP—are inserted in the plasmid expression vectors.

For example, the nucleotide sequences are inserted corresponding to the amino acid sequences (SEQ ID NO. 2) IEQEEGLNRS, or (SEQ ID NO. 11) IEQSIEQEEGLNRS and (SEQ ID NO. 3) MSEYNATQSDYRER and also the entire N-terminal portion of Syntaxin 1a is inserted in the bacterial expression vector pTAT. The particular nature of this vector lies in the fact that the fusion protein that the bacteria synthesize contains different tags which, starting from the N-terminal portion, are: 6×His, the sequence Tat= (SEQ ID NO. 4) GRKKRRQRRRPP and the tag Human influenza hemagglutinin (HA). Except for the sequence Tat that serves for rendering the synthesized protein cell permeable, the other tags are useful for the recognition of the exogenous protein by means of specific antibodies.

Preparation of Plasmids for Cellular Expression and Protein Purification from Bacterial Synthesis in Plasmid Hereinbelow, several examples are described relative to the preparation of bacterial strains containing the plasmid vectors comprising the peptide system that is the object of the present description. The quantities of the substances, indicated hereinbelow, are only reported as a non-limiting example. In the course of the present description, it is therefore assumed that the average man skilled in the art understands the possibility to use even different quantities, so as long as the ratios between the reagents are respected as in the following examples.

The lentiviral plasmid—pGEX-4 or pTAT or p-EGFP-C1 or pc-DNA—containing the above-described sequences is to be inserted in E. coli bacteria, e.g. strain DH5 alpha or BL21 and chemically competent derivatives (rosetta). Then, 5 µg of Plasmid DNA (p-EGFP-C1 or pc-DNA) is added to 20 µl of KCM 5× (containing 0.5 M KCl; 0.15M CaCl2; 0.25 M MgCl2), 5 µl MnCl2 and H2O as needed up to 100 µl of solution. At this point, an equal volume of chemically competent DH5 alpha bacterial cells are added. They are left several minutes in ice (4° C.). A thermal shock is caused by placing the entire solution at room temperature for several minutes.

Then, a volume quantity is added equal to 600 µl of Luria Broth medium (LB) (10 g/l tryptone, 5 g/l yeast extract, 10 g/l NaCl, 15 g/l agar) heated at 37° C. containing Ampicillin 100 µg/ml, since the plasmids contain the resistance to this antibiotic. Then the solution is plated on agar with the same concentration of Ampicillin. Then, proceed with the purification of the Plasmid DNA by means of MAXI-prep commercial kits, hence used for cellular transfections or for synthesis of lentiviral particles with classical methods from the literature.

The transformation of the bacteria BL21 and derivatives is carried out with a different protocol.

5 µg of vector (pGEX-4 or pTAT) is added to 100 µl of bacteria, and then this is incubated for 30 min at 4° C. Then, a thermal shock is induced by placing the solution at 42° C. for 45 seconds. In this manner, the bacteria incorporate the plasmid. The solution is then left for 5 minutes in ice and then a quantity in volume equal to 4 times (400 µl) of LB is added. The entire solution is plated on agar containing Ampicillin and the colonies are left to grow for 12 hours at approximately 37° C.

MINI-PREP, Cut with Restriction Enzymes

Since the sequences of interest were inserted between the restriction enzymes, the bacterial growth will be tested so as to control the actual incorporation of the plasmid within the bacteria.

Then the grown colonies are extracted with sterile points and placed in 5 ml of LB with Ampicillin. After a bacterial growth at 37° C. for 5-6 h, a miniprep is prepared with the commercial kits. Then, an aliquot of DNA solution obtained from each colony is subjected to enzymatic cutting, with restriction enzymes used for subcloning (37° C. for 60 minutes).

After this, the DNA is made to run on agarose gel and the cut sequence is controlled at the photometer.

Several µl of the colony that expresses more plasmid is made to grow, in order to then prepare the glycerol stocks that are frozen at −80° C.

Growth and Induction:

From the glycerol stocks, the bacteria, coming from a single colony, are made to grow at 37° C. under stirring (250 rpm) as pre-inoculum in LB+Ampicillin (100 µg/ml). ¹⁄₅₀ of the pre-inoculum is made to grow in fresh LB+Amp (the quantity depends on the intended size of the production) at 37° C. (250 rpm) up to obtaining OD600 of 0.8-1.

0.5 mM IPTG is then added in order to induce the production of the exogenous protein.

1 ml of pre-inoculum is extracted and centrifuged at 5000 rpm for 5 minutes. The pellet is then stored at −20° C. in order to then be analyzed on SDS-PAGE gel.

The induction lasts 4-5 h at 37° C. at a speed of 250 rpm.

Then, the bacteria are centrifuged at 8000 rpm for 20 minutes at 4° C.

The supernatant is decanted and the pellet is weighted and stored at −20° C.

Lysis of the Bacteria Pellet

A Lysis Buffer is added to the pellet with the following composition (0.1M TRIS-HCl, 1 mM EDTA pH 7.5) with a proportion of 2 ml of Lysis Buffer per gram of pellet.

The pellet is then resuspended and 1.5 mg/g of Lisozyme is added (from a 10 mg/ml stock) in order to lyse the bacteria. The solution is incubated for 2 h at room temperature and stirred at 200 rpm.

The lysate is incubated for 10 minutes on ice and then sonicated with 4 pulses each of 50 second duration. Between one pulse and the next, the solution is left for 1 minute in ice.

Then, a centrifuge is executed at 12000 rpm for 20 minutes at 4° C.

The supernatant is stored and a flake of pellet is removed; such flake is broken up, making it soft.

Isolation of the Inclusion Bodies

Added to the lysate volume (after sonication) is a volume equal to ½ of Triton Buffer. Then, this is incubated for 30 minutes at room temperature with a stirring of 200 rpm. Centrifuge then for 20 minutes at 4° C. at a speed of 12000 rpm. The pellet is resuspended in Lysis Buffer. Then, Triton buffer is added in a volume equal to half the volume that is in the tube. This is then incubated at room temperature at 200 rpm. Centrifuge at 12000 rpm for 20 minutes at 4° C.

The pellet is resuspended in washing buffer and centrifuged at 12000 rpm for 20 minutes at 4° C. Wash the pellet again, another 3 or 4 times, always with washing buffer. The pellet is then stored at −20° C.

Solubilization and Dialysis

The pellet is solubilized with 5 ml/g of solubilization buffer containing 6M Guanidinium and 1 mM DTT.

After 2-3 h, the pH is adjusted to 3-4 with HCl. Centrifuge then for 20 minutes at 4° C. at 12000 rpm.

The supernatant is then dialyzed with 6M Guanidinium at pH 3-4.

The dialysis solution is changed 3 times: each washing is carried out after 3 hours and the third washing is kept the entire night at 4° C.

The dialysis solution is then changed with a sodium phosphate buffer **50 mM at pH 7 with the same mode used for the dialysis with guanidinium.

Then, at the end, an aliquot of dialyzed substance is used on acrylamide gel, with coomassie staining in which one must see the band corresponding to the synthesized protein.

The rest of the dialyzed substance is purified on an ion-exchange column.

**Preparation of the Phosphate Buffer:

Prepare a 1 M NaH2PO4 solution and a 1 M Na2HPO4 solution. The two solutions are added together and pH 7 is verified.

Purification on Ion-Exchange Column.

There are three solutions used: 50 mM pH 7 phosphate buffer; 50 mM pH 7 phosphate buffer+1M NaCl; 20% Ethanol+20% sodium acetate in H2O.

The solutions are filtered, degassed and stored at +4° C. in order to be cold at the time of use.

The invention claimed is:

1. A method for blocking N-Methyl D-Aspartate (NMDA)-induced presynaptic release of glutamate in a subject in need thereof, comprising administering to the subject an effective amount of a peptide system comprising at least one peptide blocking the presynaptic release of glutamate, wherein the peptide blocking the presynaptic release of glutamate comprises an amino acid sequence selected from SEQ ID NOs: 5 and 8.

2. The method according to claim 1, wherein the amino acids in the peptide are L-amino acids or D-amino acids.

3. The method according to claim 1, wherein the peptide system is administered as a medicament comprising the peptide system.

4. The method according to claim 1, wherein the peptide further comprises a tag sequence selected from the group consisting of HA, Glutathione S-Transferase (GST), Myc, and enhanced green fluorescent protein (EGFP).

5. The method according to claim 1, wherein the peptide system is administered as a pharmaceutical composition comprising the peptide system.

6. The method according to claim 1, wherein the peptide system is administered as a pharmaceutical composition comprising the peptide system, and wherein the pharmaceutical composition is in a form selected from the group consisting of solution, suspension, ointment, patch, tablet, and capsule.

* * * * *

SEQUENCE LISTING

```
<160> NUMBER OF SEQ ID NOS: 13

<210> SEQ ID NO 1
<211> LENGTH: 288
<212> TYPE: PRT
<213> ORGANISM: Artificial Sequence
<220> FEATURE:
<223> OTHER INFORMATION: Muridae

<400> SEQUENCE: 1

Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125
```

-continued

```
Glu Val Met Ser Glu Tyr Asn Ala Thr Gln Ser Asp Tyr Arg Glu Arg
            130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Thr Ser
                195                 200                 205

Ile Arg Glu Leu His Asp Met Phe Met Asp Met Ala Met Leu Val Glu
            210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
                260                 265                 270

Val Ile Leu Gly Ile Ile Ala Ser Thr Ile Gly Gly Ile Phe Gly
            275                 280                 285
```

<210> SEQ ID NO 2
<211> LENGTH: 10
<212> TYPE: PRT
<213> ORGANISM: Artificial Sequence
<220> FEATURE:
<223> OTHER INFORMATION: Muridae

<400> SEQUENCE: 2

```
Ile Glu Gln Glu Glu Gly Leu Asn Arg Ser
1               5                   10
```

<210> SEQ ID NO 3
<211> LENGTH: 14
<212> TYPE: PRT
<213> ORGANISM: Artificial Sequence
<220> FEATURE:
<223> OTHER INFORMATION: Muridae

<400> SEQUENCE: 3

```
Met Ser Glu Tyr Asn Ala Thr Gln Ser Asp Tyr Arg Glu Arg
1               5                   10
```

<210> SEQ ID NO 4
<211> LENGTH: 12
<212> TYPE: PRT
<213> ORGANISM: Artificial Sequence
<220> FEATURE:
<223> OTHER INFORMATION: Muridae

<400> SEQUENCE: 4

```
Gly Arg Lys Lys Arg Gln Arg Arg Arg Pro Pro
1               5                   10
```

<210> SEQ ID NO 5
<211> LENGTH: 26
<212> TYPE: PRT
<213> ORGANISM: Artificial Sequence
<220> FEATURE:
<223> OTHER INFORMATION: Muridae -continued

```
<400> SEQUENCE: 5

Gly Arg Lys Lys Arg Arg Gln Arg Arg Pro Pro Ile Glu Gln Ser
1               5                   10                  15

Ile Glu Gln Glu Glu Gly Leu Asn Arg Ser
            20                  25

<210> SEQ ID NO 6
<211> LENGTH: 26
<212> TYPE: PRT
<213> ORGANISM: Artificial Sequence
<220> FEATURE:
<223> OTHER INFORMATION: Muridae

<400> SEQUENCE: 6

Ile Glu Gln Ser Ile Glu Gln Glu Glu Gly Leu Asn Arg Ser Gly Arg
1               5                   10                  15

Lys Lys Arg Arg Gln Arg Arg Pro Pro
            20                  25

<210> SEQ ID NO 7
<211> LENGTH: 26
<212> TYPE: PRT
<213> ORGANISM: Artificial Sequence
<220> FEATURE:
<223> OTHER INFORMATION: Muridae

<400> SEQUENCE: 7

Pro Pro Arg Arg Arg Gln Arg Arg Lys Lys Arg Gly Ile Glu Gln Ser
1               5                   10                  15

Ile Glu Gln Glu Glu Gly Leu Asn Arg Ser
            20                  25

<210> SEQ ID NO 8
<211> LENGTH: 26
<212> TYPE: PRT
<213> ORGANISM: Artificial Sequence
<220> FEATURE:
<223> OTHER INFORMATION: Muridae

<400> SEQUENCE: 8

Gly Arg Lys Lys Arg Arg Gln Arg Arg Pro Pro Met Ser Glu Tyr
1               5                   10                  15

Asn Ala Thr Gln Ser Asp Tyr Arg Glu Arg
            20                  25

<210> SEQ ID NO 9
<211> LENGTH: 26
<212> TYPE: PRT
<213> ORGANISM: Artificial Sequence
<220> FEATURE:
<223> OTHER INFORMATION: Muridae

<400> SEQUENCE: 9

Met Ser Glu Tyr Asn Ala Thr Gln Ser Asp Tyr Arg Glu Arg Gly Arg
1               5                   10                  15

Lys Lys Arg Arg Gln Arg Arg Pro Pro
            20                  25

<210> SEQ ID NO 10
<211> LENGTH: 26
<212> TYPE: PRT
<213> ORGANISM: Artificial Sequence
<220> FEATURE:
<223> OTHER INFORMATION: Muridae
```

```
<400> SEQUENCE: 10

Pro Pro Arg Arg Arg Gln Arg Arg Lys Lys Arg Gly Met Ser Glu Tyr
1               5                   10                  15

Asn Ala Thr Gln Ser Asp Tyr Arg Glu Arg
            20                  25

<210> SEQ ID NO 11
<211> LENGTH: 14
<212> TYPE: PRT
<213> ORGANISM: Artificial Sequence
<220> FEATURE:
<223> OTHER INFORMATION: Muridae

<400> SEQUENCE: 11

Ile Glu Gln Ser Ile Glu Gln Glu Gly Leu Asn Arg Ser
1               5                   10

<210> SEQ ID NO 12
<211> LENGTH: 300
<212> TYPE: PRT
<213> ORGANISM: Artificial Sequence
<220> FEATURE:
<223> OTHER INFORMATION: Muridae

<400> SEQUENCE: 12

Gly Arg Lys Lys Arg Gln Arg Arg Pro Pro Met Lys Asp Arg
1               5                   10                  15

Thr Gln Glu Leu Arg Thr Ala Lys Asp Ser Asp Asp Asp Val
            20                  25                  30

Thr Val Thr Val Asp Arg Asp Arg Phe Met Asp Glu Phe Phe Glu Gln
            35                  40                  45

Val Glu Glu Ile Arg Gly Phe Ile Asp Lys Ile Ala Glu Asn Val Glu
        50                  55                  60

Glu Val Lys Arg Lys His Ser Ala Ile Leu Ala Ser Pro Asn Pro Asp
65                  70                  75                  80

Glu Lys Thr Lys Glu Glu Leu Glu Glu Leu Met Ser Asp Ile Lys Lys
                85                  90                  95

Thr Ala Asn Lys Val Arg Ser Lys Leu Lys Ser Ile Glu Gln Ser Ile
            100                 105                 110

Glu Gln Glu Glu Gly Leu Asn Arg Ser Ser Ala Asp Leu Arg Ile Arg
        115                 120                 125

Lys Thr Gln His Ser Thr Leu Ser Arg Lys Phe Val Glu Val Met Ser
    130                 135                 140

Glu Tyr Asn Ala Thr Gln Ser Asp Tyr Arg Glu Arg Cys Lys Gly Arg
145                 150                 155                 160

Ile Gln Arg Gln Leu Glu Ile Thr Gly Arg Thr Thr Thr Ser Glu Glu
                165                 170                 175

Leu Glu Asp Met Leu Glu Ser Gly Asn Pro Ala Ile Phe Ala Ser Gly
            180                 185                 190

Ile Ile Met Asp Ser Ser Ile Ser Lys Gln Ala Leu Ser Glu Ile Glu
        195                 200                 205

Thr Arg His Ser Glu Ile Ile Lys Leu Glu Thr Ser Ile Arg Glu Leu
    210                 215                 220

His Asp Met Phe Met Asp Met Ala Met Leu Val Glu Ser Gln Gly Glu
225                 230                 235                 240

Met Ile Asp Arg Ile Glu Tyr Asn Val Glu His Ala Val Asp Tyr Val
                245                 250                 255
```

```
Glu Arg Ala Val Ser Asp Thr Lys Lys Ala Val Lys Tyr Gln Ser Lys
            260                 265                 270

Ala Arg Arg Lys Lys Ile Met Ile Ile Ile Cys Cys Val Ile Leu Gly
        275                 280                 285

Ile Ile Ile Ala Ser Thr Ile Gly Gly Ile Phe Gly
    290                 295                 300

<210> SEQ ID NO 13
<211> LENGTH: 22
<212> TYPE: PRT
<213> ORGANISM: Artificial Sequence
<220> FEATURE:
<223> OTHER INFORMATION: Muridae

<400> SEQUENCE: 13

Gly Arg Lys Lys Arg Arg Gln Arg Arg Pro Pro Ile Glu Gln Glu
1               5                   10                  15

Glu Gly Leu Asn Arg Ser
            20
```